US008349861B2

(12) United States Patent
Hopf

(10) Patent No.: US 8,349,861 B2
(45) Date of Patent: Jan. 8, 2013

(54) METHODS FOR IDENTIFICATION OF JAK KINASE INTERACTING MOLECULES AND FOR THE PURIFICATION OF JAK KINASES

(75) Inventor: Carsten Hopf, Mannheim (DE)

(73) Assignee: Cellzome AG, Heidelberg (DE)

( * ) Notice: Subject to any disclaimer, the term of this patent is extended or adjusted under 35 U.S.C. 154(b) by 287 days.

(21) Appl. No.: 12/742,585

(22) PCT Filed: Nov. 11, 2008

(86) PCT No.: PCT/EP2008/009498
§ 371 (c)(1),
(2), (4) Date: Oct. 21, 2010

(87) PCT Pub. No.: WO2009/062658
PCT Pub. Date: May 22, 2009

(65) Prior Publication Data
US 2011/0039718 A1  Feb. 17, 2011

Related U.S. Application Data

(60) Provisional application No. 61/073,591, filed on Jun. 18, 2008.

(30) Foreign Application Priority Data

Nov. 12, 2007 (EP) ..................................... 07021898

(51) Int. Cl.
C07D 401/14 (2006.01)
C07D 403/14 (2006.01)
A61K 31/5355 (2006.01)
A61K 31/305 (2006.01)

(52) U.S. Cl. ...................................... 514/275; 544/324
(58) Field of Classification Search .................. 544/324; 514/275
See application file for complete search history.

(56) References Cited

U.S. PATENT DOCUMENTS

2006/0270694 A1  11/2006  Wong

FOREIGN PATENT DOCUMENTS

| WO | WO 02/059110 | 8/2002 |
|----|--------------|--------|
| WO | WO 2006/134056 | 12/2006 |
| WO | WO 2007/064753 | 6/2007 |
| WO | WO 2010/042246 | 4/2010 |

OTHER PUBLICATIONS

Anieto et al., "Chapter 4.3 Subcellular Fractionation of Tissue Culture Cells," in *Current Protocols in Protein Science*, Editors: John.E. Coligan, Ben M. Dunn, Hidde L. Ploegh, David W. Speicher, Paul T. Wingfield; Wilev, ISBN: 0-471-14098-8 (2003).
Ausubel et al., "Chapter 11 Immunology," pp. 11-1 to 11-30 in: *Short Protocols in Molecular Biology*. Fourth Edition, Wiley, New York, (1999).
Biddison, W.E., "Chapter 2.2 Preparation and Culture of Human Lymphocytes," in *Current Protocols in Cell Biology*, John Wiley & Sons, Inc. (1998).
Breinbauer et al., "Natural Product Guided Compound Library Development," *Curr. Med. Chem.* 9:2129-2145 (2002).
Castle, J. David., "Chapter 4.2 Purification of Organelles from Mammalian Cells," in *Current Protocols in Protein Science*, Editors: John. E. Coligan, Ben M. Dunn, Hidde L. Ploegh, David W. Speicher, Paul T. Wingfield, Wiley, ISBN: 0-471-14098-8 (2004).
Changelian et al., "Prevention of Organ Allograft Rejection by a Specific Janus Kinase 3 Inhibitor," *Science* 302:875-888 and online supplement (2003).
Chen et al., "Development of Pyrimidine-Based Inhibitors of Janus Tyrosine Kinase 3," *Bioorg. Med. Chem. Letters* 16:5633-5638 (2006).
Edwards et al., "Solid-Phase Compound Library Synthesis in Drug Design and Development," *Curr. Onin. Drug Discov. Devel.* 5:594-605 (2002).
Fenteany et al., "Inhibition of Proteasome Activisties and Subunit-Specific Amino-Terminal Threonine Modification by Lactacystin," *Science* 268:726-731 (1995).
Fuchikami et al., "A Versatile High-Throughput Screen for Inhibitors of Lipid Kinase Activity: Development of an Immobilized Phospholipid Plate Assay for Phosphoinositide 3-Kinase γ," *J. Biomol. Screening* 7:441-450 (2002).
Goodnow, "Current Practices in Generation of Small Molecule New Leads," *J. Cell Biochem.Suppl.* 37:13-21 (2001).
Karwa and Mitra "'Sample Preparation for the Extraction, Isolation, and Purification of Nucleic Acids'; Chapter 8 in Sample Preparation Techniques in Analytical Chemistry," *Chemical Analysis* 162:331-375 (2003).
Kashem et al., "Three Mechanistically Distinct Kinase Assays Compared: Measurement of Intrinsic ATPase Activisty Identified the Most Comprehensive Set of ITK Inhibitors," *J. Biomol. Screening* 12:70-83 (2007).
Langer, "New Methods of Drug Delivery," *Science* 249:1527-1533 (1990).
Levine et al., "Role of JAK2 in the Pathogenesis and Therapy of Myeloproliferative Disorders," *Nat. Rev. Cancer.* 7: 673-683 (2007).
Li et al., "Characterization of a Highly Effective Protein Substrate for Analysis of $JAK2^{V617F}$ Activity," *Experimental Hematology* 35:1624-1632 (2007).
Macchi et al., "Mutations of JAK-3 Gene in Patients with Autosomal Severe Combined Immune Deficiency (SCID)," *Nature* 377:65-68 (1995).
Mann et al., "Analysis of Proteins and Proteomes by Mass Spectrometry," *Annual Review of Biochemistry* 70:437-473 (2001).
Melnick et al., "An Efficient Rapid System for Profiling the Cellular Activities of Molecular Libraries," *PNAS* 103:3153-3158 (2006).
Merlot et al., "Fragment Analysis in Small Molecule Discovery," *Curr. Opin. Drug. Discov. Devel.* 5:391-399 (2002).
Moger et al., "The Application of Fluorescense Lifetime Readouts in High-Throughput Screening," *J. Biomol. Screening* 11: 765-772 (2006).
Musso et al., "Regulation of JAK3 Expression in Human Monocytes: Phosphorylation in Response to Interleukins 2, 4, and 7," *Journal of Experimental Medicine* 181:1425-31 (1995).

(Continued)

*Primary Examiner* — Deepak Rao
(74) *Attorney, Agent, or Firm* — Kristina Bieker-Brady; Clark & Elbing LLP

(57) ABSTRACT

The present invention relates to immobilization compounds and methods useful for the identification of JAK interacting compounds or for the purification or identification of JAK.

21 Claims, 10 Drawing Sheets

OTHER PUBLICATIONS

Figure 1:
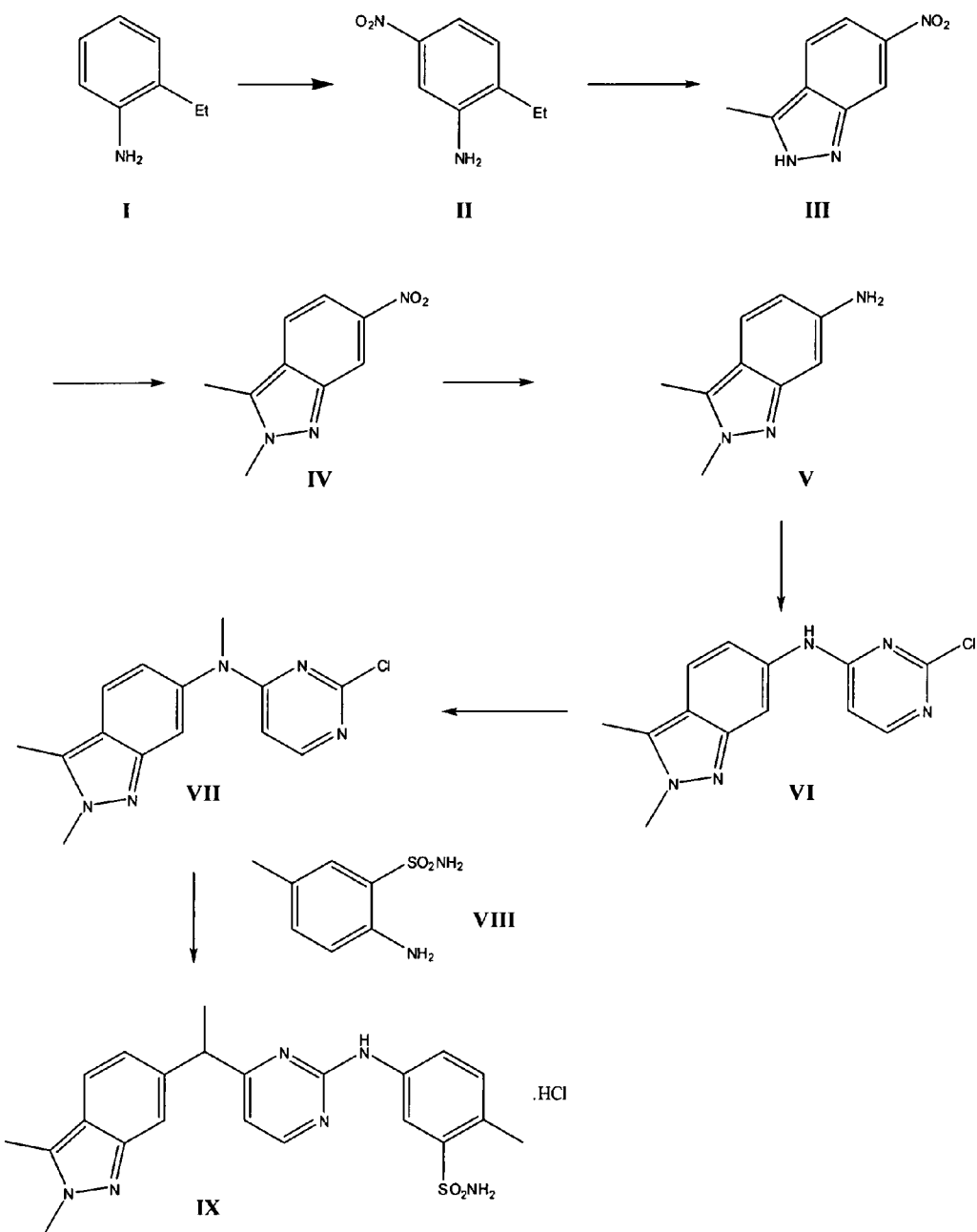

Neilson et al., "Coactivation of Janus Tyrosine Kinase (Jak)1 Positively Modulates Prolactin-Jak2 Signaling in Breast Cancer: Recruitment of ERK and Signal Transducer and Activator or Transcription (Stat)3 and Enhancement of Akt and State5a/b Pathways," *Molecular Endocrinology* 21:2218-2232 (2007).

Neubauer et al., "Jak2 Deficiency Defines an Essential Developmental Checkpoint in Definitive Hematopoiesis," *Cell* 93(3):397-409 (1998).

O'Shea et al., "Immunosuppresion: Targeting the Jak/Stat Pathway," *Nat. Rev. Drug Discov.* 3:555-64 (2004).

Papageorgiou and Wikman "Is JAK3 a New Drug Target for Immunomodulation-based Therapies?" *Trends in Pharmacological Sciences* 25:558-62 (2004).

Pardanani et al., "TG101209, a Small Molecule JAK2-Selective Kinase Inhibitor Potently Inhibits Myeloproliferative Disorder-Associated JAK2V617F and *MPLW*515L/K Mutations," *Leukemia* 21:1658-68 (2007).

Perkins et al., "Probability-Based Protein Identification by Searching Sequence Data-Bases Using Mass Snectrometry Data," *Electrophoresis* 20:3551-3567 (1999).

Petty, Howard R., "Chapter 1, Unit 5.1.1-5.1.10 Overview of the Physical State of Proteins," in: Juan S. Bonifacino, Mary Dasso, Joe B. Harford, Jennifer Lippincott-Schwartz, and Kenneth M. Yamada (eds.) *Current Protocols in Cell Biology* Copyright © 1998 by John Wiley & Sons, Inc. DOI: 1O.I002/0471143030.cbOI0Is000nline Posting Date: May 2001 Print Publication Date: Oct. 1998.

Rodig et al., "Disruption of the Jak1 Gene Demonstrates Obligatory and Nonredundant Roles of the Jaks in Cytokine-Induced Biologic Responses," *Cell* 93:373-383 (1998).

Schindler et al., "JAK-STAT Signaling: From Interferons to Cytokines," *J. Biol. Chem.* 282:20059-20063 (2007).

Scott et al., "JAK2 Exon 12 Mutations in Polycythemia Vera and Idiopathic Erythrocytosis," *N. Engl. J. Med.* 356:459-68 (2007).

Shevchenko et al., "Mass Spectrometric Sequencing of Proteins Silver-Stained Polyacrylamide Gels," *Analytical Chemistry* 68:850-858 (1996).

Subramanian, "Immunoaffinity Chromatography," *Molecular Biotechnology* 20:40-47 (2002).

Vedvik et al., "Overcoming Compound Interference in Fluorescence Polarization-Based Kinase Assays Using Far-Red Tracers," *Assay Drug Dev. Technol.* 2: 193-203 (2004).

Walters et al., "Activating Alleles of JAK3 in Acute Megakaryoblastic Leukemia," *Cancer Cell* 10:65-75 (2006).

Williams et al., "Phenotypic Variations and New Mutations in JAK2 V614F-Negative Polycythemia Vera, Erythrocytosis, and Idiopathic Myelofibrosis," *Exn.Hernatol.* 35:1641-1646 (2007).

Wingfield, Paul T., "Production of Recombinant Proteins," Chapter 5, Unit 5.0.1-5.0.3 in: *Current Protocols in Protein Science*, Editors: John. E. Coligan, Ben M. Dunn, Hidde L. Ploegh, David W. Speicher, Paul T. Wingfield; Wilev, ISBN: 0-471-14098-8 (2002).

Wu and Wu, "Receptor-Mediated In Vitro Gene Transformation by a Soluble DNA Carrier System," *J. Biol. Chem.* 262:4429-4432 (1987).

Wu et al., "Comparative Study of Three Proteomic Quantitative Methods, DIGE, cICAT, and iTRAQ, Using 2D Gel- or LC-MALDI TOF/TOF," *J. Proteome Res.* 5:651-658 (2006).

Yamaoka et al., "The Janus Kinases (Jaks)," *Genome Biology* 5(12): 253 (2004).

Yang et al., "Simplified Staurosporine Analogs as Potent JAK3 Inhibitors," *Bioorg. Med. Chem. Letters* 17: 326-331 (2007).

Zaman et al., "Fluorescence Assays for High-Throughput Screening of Protein Kinases," *Comb. Chem. High Throughput Screen* 6: 313-320 (2003).

Zaman et al., "Enzyme Fragment Complementation Binding Assay for P38Alpha Mitogen-Activated Protein Kinase to Study the Binding Kinetics of Enzyme Inhibitors," *Assay Drug Dev. Technol.* 4:411-420 (2006).

Zhang et al., "Time-Resolved Forster Resonance Energy Transfer Assays for the Binding of Nucleotide and Protein Substrates to P38Alpha Protein Kinase," *Analytical Biochemistry* 343:76-83 (2005).

Zhu et al., "Growth Hormone Stimulates the Tyrosine Phosphorylation and Association of P125 Focal Adhesion Kinase (FAK) with JAK2. Fak is not Required for Stat-Mediated Transcription," *J. Biol. Chem.* 273:10682-10689 (1998).

Figure 6

```
   1 MQYLNIKEDC NAMAFCAKMR SSKKTEVNLE APEPGVEVIF YLSDREPLRL
  51 GSGEYTAEEL CIRAAQACRI SPLCHNLFAL YDENTKLWYA PNRTITVDDK
 101 MSLRLHYRMR FYFTNWHGTN DNEQSVWRHS PKKQKNGYEK KKIPDATPLL
 151 DASSLEYLFA QGQYDLVKCL APIRDPKTEQ DGHDIENECL GMAVLAISHY
 201 AMMKKMQLPE LPKDISYKRY IPETLNKSIR QRNLLTRMRI NNVFKDFLKE
 251 FNNKTICDSS VSTHDLKVKY LATLETLTKH YGAEIFETSM LLISSENEMN
 301 WFHSNDGGNV LYYEVMVTGN LGIQWRHKPN VVSVEKEKNK LKRKKLENKH
 351 KKDEEKNKIR EEWNNFSYFP EITHIVIKES VVSINKQDNK KMELKLSSHE
 401 EALSFVSLVD GYFRLTADAH HYLCTDVAPP LIVHNIQNGC HGPICTEYAI
 451 NKLRQEGSEE GMYVLRWSCT DFDNILMTVT CFEKSEQVQG AQKQFKNFQI
 501 EVQKGRYSLH GSDRSFPSLG DLMSHLKKQI LRTDNISFML KRCCQPKPRE
 551 ISNLLVATKK AQEWQPVYPM SQLSFDRILK KDLVQGEHLG RGTRTHIYSG
 601 TLMDYKDDEG TSEEKKIKVI LKVLDPSHRD ISLAFFEAAS MMRQVSHKHI
 651 VYLYGVCVRD VENIMVEEFV EGGPLDLFMH RKSDVLTTPW KFKVAKQLAS
 701 ALSYLEDKDL VHGNVCTKNL LLAREGIDSE CGPFIKLSDP GIPITVLSRQ
 751 ECIERIPWIA PECVEDSKNL SVAADKWSFG TTLWEICYNG EIPLKDKTLI
 801 EKERFYESRC RPVTPSCKEL ADLMTRCMNY DPNQRPFFRA IMRDINKLEE
 851 QNPDIVSEKK PATEVDPTHF EKRFLKRIRD LGEGHFGKVE LCRYDPEGDN
 901 TGEQVAVKSL KPESGGNHIA DLKKEIEILR NLYHENIVKY KGICTEDGGN
 951 GIKLIMEFLP SGSLKEYLPK NKNKINLKQQ LKYAVQICKG MDYLGSRQYV
1001 HRDLAARNVL VESEHQVKIG DFGLTKAIET DKEYYTVKDD RDSPVFWYAP
1051 ECLMQSKFYI ASDVWSFGVT LHELLTYCDS DSSPMALFLK MIGPTHGQMT
1101 VTRLVNTLKE GKRLPCPPNC PDEVYQLMRK CWEFQPSNRT SFQNLIEGFE
1151 ALLK
```

Figure 7

```
   1 MGMACLTMTE MEGTSTSSIY QNGDISGNAN SMKQIDPVLQ VYLYHSLGKS
  51 EADYLTFPSG EYVAEEICIA ASKACGITPV YHNMFALMSE TERIWYPPNH
 101 VFHIDESTRH NVLYRIRFYF PRWYCSGSNR AYRHGISRGA EAPLLDDFVM
 151 SYLFAQWRHD FVHGWIKVPV THETQEECLG MAVLDMMRIA KENDQTPLAI
 201 YNSISYKTFL PKCIRAKIQD YHILTRKRIR YRFRRFIQQF SQCKATARNL
 251 KLKYLINLET LQSAFYTEKF EVKEPGSGPS GEEIFATIII TGNGGIQWSR
 301 GKHKESETLT EQDLQLYCDF PNIIDVSIKQ ANQEGSNESR VVTIHKQDGK
 351 NLEIELSSLR EALSFVSLID GYYRLTADAH HYLCKEVAPP AVLENIQSNC
 401 HGPISMDFAI SKLKKAGNQT GLYVLRCSPK DFNKYFLTFA VERENVIEYK
 451 HCLITKNENE EYNLSGTKKN FSSLKDLLNC YQMETVRSDN IIFQFTKCCP
 501 PKPKDKSNLL VFRTNGVSDV PTSPTLQRPT HMNQMVFHKI RNEDLIFNES
 551 LGQGTFTKIF KGVRREVGDY GQLHETEVLL KVLDKAHRNY SESFFEAASM
 601 MSKLSHKHLV LNYGVCVCGD ENILVQEFVK FGSLDTYLKK NKNCINILWK
 651 LEVAKQLAWA MHFLEENTLI HGNVCAKNIL LIREEDRKTG NPPFIKLSDP
 701 GISITVLPKD ILQERIPWVP PECIENPKNL NLATDKWSFG TTLWEICSGG
 751 DKPLSALDSQ RKLQFYEDRH QLPAPKWAEL ANLINNCMDY EPDFRPSFRA
 801 IIRDLNSLFT PDYELLTEND MLPNMRIGAL GFSGAFEDRD PTQFEERHLK
 851 FLQQLGKGNF GSVEMCRYDP LQDNTGEVVA VKKLQHSTEE HLRDFEREIE
 901 ILKSLQHDNI VKYKGVCYSA GRRNLKLIME YLPYGSLRDY LQKHKERIDH
 951 IKLLQYTSQI CKGMEYLGTK RYIHRDLATR NILVENENRV KIGDFGLTKV
1001 LPQDKEYYKV KEPGESPIFW YAPESLTESK FSVASDVWSF GVVLYELFTY
1051 IEKSKSPPAE FMRMIGNDKQ GQMIVFHLIE LLKNNGRLPR PDGCPDEIYM
1101 IMTECWNNNV NQRPSFRDLA LRVDQIRDNM AG
```

Figure 8

```
   1 MAPPSEETPL IPQRSCSLLS TEAGALHVLL PARGPGPPQR LSFSFGDHLA
  51 EDLCVQAAKA SGILPVYHSL FALATEDLSC WFPPSHIFSV EDASTQVLLY
 101 RIRFYFPNWF GLEKCHRFGL RKDLASAILD LPVLEHLFAQ HRSDLVSGRL
 151 PVGLSLKEQG ECLSLAVLDL ARMAREQAQR PGELLKTVSY KACLPPSLRD
 201 LIQGLSFVTR RRIRRTVRRA LRRVAACQAD RHSLMAKYIM DLERLDPAGA
 251 AETFHVGLPG ALGGHDGLGL LRVAGDGGIA WTQGEQEVLQ PFCDFPEIVD
 301 ISIKQAPRVG PAGEHRLVTV TRTDNQILEA EFPGLPEALS FVALVDGYFR
 351 LTTDSQHFFC KEVAPPRLLE EVAEQCHGPI TLDFAINKLK TGGSRPGSYV
 401 LRRSPQDFDS FLLTVCVQNP LGPDYKGCLI RRSPTGTFLL VGLSRPHSSL
 451 RELLATCWDG GLHVDGVAVT LTSCCIPRPK EKSNLIVVQR GHSPPTSSLV
 501 QPQSQYQLSQ MTFHKIPADS LEWHENLGHG SFTKIYRGCR HEVVDGEARK
 551 TEVLLKVMDA KHKNCMESFL EAASLMSQVS YRHLVLLHGV CMAGDSTMVQ
 601 EFVHLGAIDM YLRKRGHLVP ASWKLQVVKQ LAYALNYLED KGLPHGNVSA
 651 RKVLLAREGA DGSPPFIKLS DPGVSPAVLS LEMLTDRIPW VAPECLREAQ
 701 TLSLEADKWG FGATVWEVFS GVTMPISALD PAKKLQFYED RQQLPAPKWT
 751 ELALLIQQCM AYEPVQRPSF RAVIRDLNSL ISSDYELLSD PTPGALAPRD
 801 GLWNGAQLYA CQDPTIFEER HLKYISQLGK GNFGSVELCR YDPLGDNTGA
 851 LVAVKQLQHS GPDQQRDFQR EIQILKALHS DFIVKYRGVS YGPGRQSLRL
 901 VMEYLPSGCL RDFLQRHRAR LDASRLLLYS SQICKGMEYL GSRRCVHRDL
 951 AARNILVESE AHVKIADFGL AKLLPLDKDY YVVREPGQSP IFWYAPESLS
1001 DNIFSRQSDV WSFGVVLYEL FTYCDKSCSP SAEFLRMMGC ERDVPALCRL
1051 LELLEEGQRL PAPPACPAEV HELMKLCWAP SPQDRPSFSA LGPQLDMLWS
1101 GSRGCETHAF TAHPEGKHHS LSFS
```

Figure 9

```
   1 MPLRHWGMAR GSKPVGDGAQ PMAAMGGLKV LLHWAGPGGG EPWVTFSESS
  51 LTAEEVCIHI AHKVGITPPC FNLFALFDAQ AQVWLPPNHI LEIPRDASLM
 101 LYFRIRFYFR NWHGMNPREP AVYRCGPPGT EASSDQTAQG MQLLDPASFE
 151 YLFEQGKHEF VNDVASLWEL STEEEIHHFK NESLGMAFLH LCHLALRHGI
 201 PLEEVAKKTS FKDCIPRSFR RHIRQHSALT RLRLRNVFRR FLRDFQPGRL
 251 SQQMVMVKYL ATLERLAPRF GTERVPVCHL RLLAQAEGEP CYIRDSGVAP
 301 TDPGPESAAG PPTHEVLVTG TGGIQWWPVE EEVNKEEGSS GSSGRNPQAS
 351 LFGKKAKAHK AVGQPADRPR EPLWAYFCDF RDITHVVLKE HCVSIHRQDN
 401 KCLELSLPSR AAALSFVSLV DGYFRLTADS SHYLCHEVAP PRLVMSIRDG
 451 IHGPLLEPFV QAKLRPEDGL YLIHWSTSHP YRLILTVAQR SQAPDGMQSL
 501 RLRKFPIEQQ DGAFVLEGWG RSFPSVRELG AALQGCLLRA GDDCFSLRRC
 551 CLPQPGETSN LIIMRGARAS PRTLNLSQLS FHRVDQKEIT QLSHLGQGTR
 601 TNVYEGRLRV EGSGDPEEGK MDDEDPLVPG RDRGQELRVV LKVLDPSHHD
 651 IALAFYETAS LMSQVSHTHL AFVHGVCVRG PENIMVTEYV EHGPLDVWLR
 701 RERGHVPMAW KMVVAQQLAS ALSYLENKNL VHGNVCGRNI LLARLGLAEG
 751 TSPFIKLSDP GVGLGALSRE ERVERIPWLA PECLPGGANS LSTAMDKWGF
 801 GATLLEICFD GEAPLQSRSP SEKEHFYQRQ HRLPEPSCPQ LATLTSQCLT
 851 YEPTQRPSFR TILRDLTRLQ PHNLADVLTV NPDSPASDPT VFHKRYLKKI
 901 RDLGEGHFGK VSLYCYDPTN DGTGEMVAVK ALKADCGPQH RSGWKQEIDI
 951 LRTLYHEHII KYKGCCEDQG EKSLQLVMEY VPLGSLRDYL PRHSIGLAQL
1001 LLFAQQICEG MAYLHAQHYI HRDLAARNVL LDNDRLVKIG DFGLAKAVPE
1051 GHEYYRVRED GDSPVFWYAP ECLKEYKFYY ASDVWSFGVT LYELLTHCDS
1101 SQSPPTKFLE LIGIAQGQMT VLRLTELLER GERLPRPDKC PCEVYHLMKN
1151 CWETEASFRP TFENLIPILK TVHEKYQGQA PSVFSVC
```

METHODS FOR IDENTIFICATION OF JAK KINASE INTERACTING MOLECULES AND FOR THE PURIFICATION OF JAK KINASES

CROSS REFERENCE TO RELATED APPLICATIONS

This application is the U.S. National Stage of International Application PCT/EP2008/009498, filed Nov. 11, 2008, which claims priority from European patent application number 07021898.7, filed Nov. 12, 2007, and U.S. Provisional application No. 61/073,591, filed Jun. 18, 2008.

The present invention relates to immobilization compounds and methods useful for the identification of JAK kinase interacting molecules and for the purification of JAK. Furthermore, the present invention relates to pharmaceutical compositions comprising said interacting molecules e.g. for the treatment of cancer, metabolic diseases or autoimmune/inflammatory disorders and to methods for the diagnosis of myeloproliferative diseases.

Kinases catalyze the phosphorylation of proteins, lipids, sugars, nucleosides and other cellular metabolites and play key roles in all aspects of eukaryotic cell physiology. Especially, protein kinases and lipid kinases participate in the signaling events which control the activation, growth, differentiation and survival of cells in response to extracellular mediators or stimuli such as growth factors, cytokines or chemokines. In general, protein kinases are classified in two groups, those that preferentially phosphorylate tyrosine residues and those that preferentially phosphorylate serine and/or threonine residues.

Inappropriately high protein kinase activity is involved in many diseases including cancer, metabolic diseases and autoimmune/inflammatory disorders. This can be caused either directly or indirectly by the failure of control mechanisms due to mutation, overexpression or inappropriate activation of the enzyme. In all of these instances, selective inhibition of the kinase is expected to have a beneficial effect.

One group of kinases that has become a recent focus of drug discovery is the Janus kinase (JAK) family of non-receptor tyrosine kinases. In mammals, the family has four members, JAK1, JAK2, JAK3 and Tyrosine kinase 2 (TYK2). Each protein has a kinase domain and a catalytically inactive pseudo-kinase domain. The JAK proteins bind to cytokine receptors through their amino-terminal FERM (Band-4.1, ezrin, radixin, moesin) domains. After the binding of cytokines to their receptors, JAKs are activated and phosphorylate the receptors, thereby creating docking sites for signalling molecules, especially for members of the signal transducer and activator of transcription (Stat) family (Yamaoka et al., 2004. The Janus kinases (Jaks). Genome Biology 5(12): 253).

In mammals, JAK1, JAK2 and TYK2 are ubiquitously expressed. By contrast, the expression of JAK3 is predominantly in hematopoietic cells and it is highly regulated with cell development and activation (Musso et al., 1995. 181(4): 1425-31).

The study of JAK-deficient cell lines and gene-targeted mice has revealed the essential, nonredundant functions of JAKs in cytokine signalling. JAK1 knockout mice display a perinatal lethal phenotype, probably related to the neurological effects that prevent them from sucking (Rodig et al., 1998. Cell 93(3):373-83). Deletion of the JAK2 gene results in embryonic lethality at embryonic day 12.5 as a result of a defect in erythropoiesis (Neubauer et al., 1998. Cell 93(3): 397-409). Interestingly, JAK3 deficiency was first identified in humans with autosomal recessive severe combined immunodeficiency (SCID) (Macchi et al., 1995. Nature 377(6544): 65-68). Jak3 knockout mice too exhibit SCID but do not display non-immune defects, suggesting that an inhibitor of JAK3 as an immunosuppressant would have restricted effects in vivo and therefore presents a promising drug for immunosuppression (Papageorgiou and Wikman 2004, Trends in Pharmacological Sciences 25(11):558-62).

Several JAK3 inhibitors have been reported in the literature (O'Shea et al., 2004. Nat. Rev. Drug Discov. 3(7):555-64). A selective and potent JAK3 inhibitor (CP-690,550) against JAK3 was reported that showed efficacy in an animal model of organ transplantation (Changelian et al., 2003, Science 302(5646):875-888).

Activating mutations for JAK3 have been observed in acute megakaryoblastic leukemia (AMKL) patients (Walters et al., 2006. Cancer Cell 10(1):65-75). These mutated forms of JAK3 can transform Ba/F3 cells to factor-independent growth and induce features of megakaryoblastic leukemia in a mouse model.

More recently it has been reported that JAK2 plays a critical role in the pathogenesis of myeloproliferative diseases (MPD) and presents a promising drug target (Levine et al., 2007. Nat. Rev. Cancer. 7(9): 673-683). Almost all patients with polycytemia vera (PV) and a significant number of patients with essential thrombocythemia (ET) and primary myelofibrosis (PMF) have constitutively active JAK2 with the V617F mutation (substitution of valine for phenylalanine at codon 617). JAK2V617F is a constitutively active tyrosine kinase that activates Stat proteins, mitogen activated protein kinase (MAPK) and phospatidylinositol 3-kinase (PI3K) signaling pathways and transforms haemotopoietic progenitor cells. The identification of JAK2V617F had a significant impact on the classification, diagnosis and prognosis of PV, ET and PMF. In addition, gain-of-function mutations in JAK2 exon 12 were observed in some patients with JAK2V617F-negative myeloproliferative disorders, suggesting that JAK is central to the pathogenesis (Scott et al., 2007. N. Engl. J. Med. 356(5):459-68; Williams et al., 2007. Exp. Hematol. 35:1641-1646). The discovery of JAK2V617F has prompted the search for selective JAK2 inhibitors for the treatment of PV, ET and PMF (Pardanani et al., 2007. Leukemia 21(8): 1658-68).

One prerequisite for the identification and characterization of JAK inhibitors is the provision of suitable assays, preferably using physiological forms of the protein target. In the art, several strategies have been proposed to address this issue.

Conventionally, JAK kinase activity can be measured using purified or recombinant enzyme in a solution-based assay with protein or peptide substrates (Changelian et al., 2003, Science 302(5646):875-888 and online supplement; Yang et al., 2007. Bioorg. Med. Chem. Letters 17(2): 326-331). This type of assay can be used to identify JAK inhibitors, but also to assess inhibitor selectivity by testing an inhibitor against all members of the JAK family.

Another assay for measuring the kinase activity of the V617F JAK2 mutant was described (Li et al., 2007. Experimental Hematology 35:1624-1632). In this protocol a GST-JAK5 fusion protein which comprises the autophosphorylation sites of human JAK2 was used as a substrate for JAK2 and JAK2V617F.

A cell-based assay (TF-1 cell proliferation) was described to assess the inhibitory activity of small molecule drugs toward JAK2 or JAK3-dependent signal transduction (Chen et al., 2006. Bioorg. Med. Chem. Letters 16(21): 5633-5638).

Another cellular assay for the identification and profiling of tyrosine kinase inhibitors was reported (Melnick et al., 2006. PNAS 103, 3153-3158). In this system Tel-tyrosine kinase fusion proteins were stably expressed after transfection into Ba/F3 cells, a murine interleukin-3 dependent pro-B cell line. Cell lines for JAK2, JAK3 and TYK2 were established and used for the profiling of kinase inhibitors.

In view of the above, there is a need for providing effective tools and methods for the identification and selectivity profiling of JAK interacting compounds as well as for the purification of JAK.

The present invention relates inter alia to an immobilization compound of formula (I)

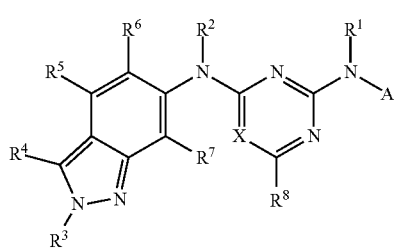

or a salt thereof, wherein
X is N or C($R^9$);
$R^1$, $R^2$, $R^3$ are independently selected from the group consisting of H or $C_{1-4}$ alkyl;
$R^4$, $R^5$, $R^6$, $R^7$, $R^8$, $R^9$ are independently selected from the group consisting of H; halogen; $C_{1-4}$ alkyl; $OC_{1-4}$ alkyl; OH, wherein $C_{1-4}$ alkyl is optionally substituted with one or more $R^{10}$;
$R^{10}$ is halogen, OH or $C_{1-4}$ alkyl; and
A is

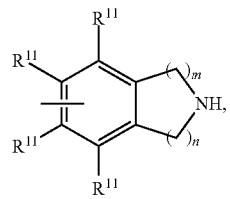

wherein each $R^{11}$ is independently selected from the group consisting of H; halogen; $C_{1-4}$ alkyl; $OC_{1-4}$ alkyl; OH, wherein $C_{1-4}$ alkyl is optionally substituted with one or more $R^{10}$;
n is 0, 1 or 2; and m is 1 or 2.

In case a variable or substituent can be selected from a group of different variants and such variable or substituent occurs more than once the respective variants can be the same or different.

Within the meaning of the present invention the terms are used as follows:

"Alkyl" means a straight-chain or branched carbon chain that may contain double or triple bonds. It is generally preferred that alkyl doesn't contain double or triple bonds. Thus, the term "alkyl" includes within the meaning of the present invention alkyl groups as well as alkenyl and alkinyl groups. Each hydrogen of an alkyl carbon may be replaced by a substituent.

"$C_{1-4}$ alkyl" means an alkyl chain having 1-4 carbon atoms, e.g. methyl, ethyl, —CH═CH$_2$, n-propyl, isopropyl, —CH═CH—CH$_3$, —CH$_2$—CH═CH$_2$, n-butyl, isobutyl, —CH═CH—CH$_2$—CH$_3$, —CH═CH—CH═CH$_2$, sec-butyl tert-butyl. Preferably, $C_{1-4}$ alkyl is methyl, ethyl, n-propyl, isopropyl, n-butyl, isobutyl, sec-butyl or tert-butyl. Each hydrogen of a $C_{1-4}$ alkyl carbon may be replaced by a substituent.

"Halogen" means fluoro, chloro, bromo or iodo. It is generally preferred that halogen is fluoro or chloro.

The immobilization compounds claimed in the present invention have been named as "immobilization compounds" due to their preferred use in the preparation of immobilization products as described below. However, other possible uses, e.g. as a soluble competitor in assays or as a labelled probe, are also explicitly included within the present invention.

In case the immobilization compounds according to formula (I) contain one or more acidic or basic groups, the invention also comprises their corresponding salts. Thus, the immobilization compounds of the formula (I) which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Immobilization compounds of the formula (I) which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the immobilization compounds of the formula (I) simultaneously contain acidic and basic groups in the molecule, the invention also includes, in addition to the salt forms mentioned, inner salts or betaines (zwitterions). The respective salts according to the formula (I) can be obtained by customary methods which are known to the person skilled in the art like, for example by contacting these with an organic or inorganic acid or base in a solvent or dispersant, or by anion exchange or cation exchange with other salts.

The present invention furthermore includes all solvates of the immobilization compounds according to the invention.

As it can be taken from the Examples, immobilization compounds falling under formula (I) have been shown to bind to JAK kinases, which makes them useful tools in the context of assays for the identification of JAK interacting compounds.

Preferred immobilization compounds of formula (I) are those immobilization compounds in which one or more of the residues contained therein have the meanings given below, with all combinations of preferred substituent definitions being a subject of the present invention. With respect to all preferred immobilization compounds of the formulae (I) the present invention also includes all tautomeric and stereoisomeric forms and mixtures thereof in all ratios.

In preferred embodiments of the present invention, the substituents mentioned below independently have the following meaning. Hence, one or more of these substituents can have the preferred or more preferred meanings given below.

Preferably, X is CH;
Preferably, $R^1$, $R^2$, $R^3$ are independently selected from the group consisting of H, and CH$_3$. More preferred R' is H; $R^2$ is CH$_3$; $R^3$ is CH$_3$.
Preferably, $R^4$, $R^5$, $R^6$, $R^7$, $R^8$, $R^9$ are H.
Preferably, each $R^{11}$ is H.
Preferably, n is 1.
Preferably, m is 2.

Preferred immobilization compounds of formula (I) of the present invention are selected from the group consisting of

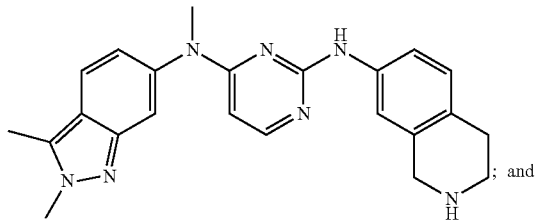
; and

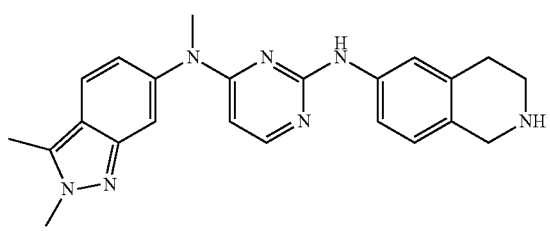

or a mixture of both, preferably in the form of a hydrohalogenide, especially as hydrochloride.

The immobilization compounds of the present invention can be prepared by methods well known in the art. Exemplary analogous routes for the synthesis are described in, e.g., WO-A 02/059110 or WO-A 2007/064753.

The invention further relates to a method for the preparation of an immobilization product, wherein at least one immobilization compound according to the invention is immobilized on a solid support. Such immobilization products obtainable according to the method of the invention are e.g. useful in the methods of the invention for the identification of JAK interacting compounds or in diagnostic methods for the diagnosis of myeloproliferative diseases.

According to the method of the invention, at least one immobilization compound of the invention is immobilized on a solid support. Throughout the invention, the term "solid support" relates to every undissolved support being able to immobilize a small molecule ligand on its surface.

According to the invention, the term "at least one immobilization compound" means either that at least one immobilization compound of the same type is immobilized on the solid support or that one or more different immobilization compounds (each of them either in singular or plural) may be immobilized on the solid support. Preferably, one or two different immobilization compounds are immobilized on the solid support, more preferably the preferred immobilization compounds of formula (I) of the present invention selected from the group consisting of

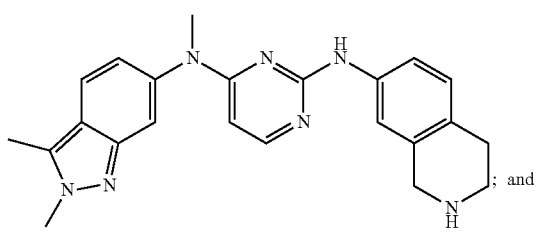
; and

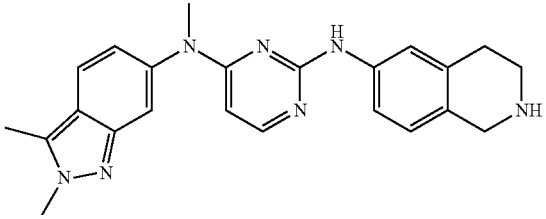

The solid support may be selected from the group consisting of agarose, modified agarose, sepharose beads (e.g. NHS-activated sepharose), latex, cellulose, and ferro- or ferrimagnetic particles.

In case that the solid support is a material comprising various entities, e.g. in case that the solid support comprises several beads or particles, it is envisaged within the present invention that, if different immobilization compounds are immobilized, on each single entity, e.g. each bead or particle, one or more different immobilization compounds are immobilized. Therefore, in case that two immobilization compounds are used, it is envisaged within the present invention that on each single entity one or two different immobilization compounds are immobilized. If no measures are taken that on one entity only one different immobilization compound is immobilized, it is very likely that on each entity all different immobilization compounds will be present.

The immobilization compound or compounds of the invention may be coupled to the solid support (and thereby immobilized) either covalently or non-covalently. Non-covalent binding includes binding via biotin affinity ligands binding to streptavidin matrices.

Preferably, the immobilization compound or compounds are covalently coupled to the solid support.

Methods for immobilizing compounds on solid supports are known in the art and further exemplified in Example 1.

In general, before the coupling, the matrixes can contain active groups such as NHS, Carbodimide etc. to enable the coupling reaction with the immobilization compound. The immobilization compound can be coupled to the solid support by direct coupling (e.g. using functional groups such as amino-, sulfhydryl-, carboxyl-, hydroxyl-, aldehyde-, and ketone groups) and by indirect coupling (e.g. via biotin, biotin being covalently attached to the immobilization product of the invention and non-covalent binding of biotin to streptavidin which is bound directly to the solid support).

The linkage to the solid support material may involve cleavable and non-cleavable linkers.

The cleavage may be achieved by enzymatic cleavage or treatment with suitable chemical methods.

Therefore, according to a preferred embodiment of the invention, the immobilization product results from a covalent direct or linker mediated attachment of the at least one immobilization compound of the invention to the solid support.

The linker may be a $C_{1-10}$ alkylene group, which is optionally interrupted by one or more atoms or functional groups selected from the group consisting of S, O, NH, C(O)O, C(O), and C(O)NH and wherein the linker is optionally substituted with one or more substituents independently selected from the group consisting of halogen, OH, $NH_2$, C(O)H, C(O)$NH_2$, $SO_3H$, $NO_2$, and CN. Alternatively, the linker may also be a $C_{1-20}$ alkylene group, optionally with the further embodiments as defined above.

The term "$C_{1-10}$ alkylene" means an alkylene chain having 1-10 carbon atoms, e.g. methylene, ethylene, —CH=CH—, —C≡C—, n-propylene and the like, wherein each hydrogen of a carbon atom may be replaced by a substituent.

The term "interrupted" means that the one or more atoms or functional groups are inserted between two carbon atoms of the alkylene chain or at the end of said chain.

Preferably, said immobilization occurs via the ring nitrogen atom of the residue A in formula (I) above. More preferred, said nitrogen atom is part of an amid functional group, so that the immobilization occurs via amid bond forming of an immobilization compound of the present invention or a mixture thereof and optionally activated carboxylic acid functional groups of the solid support. Perhaps well known protective group techniques may be required during the immobilization step.

The invention further relates to an immobilization product, obtainable by the method of the invention.

Therefore, an immobilization product which is obtainable by the method of the invention is an immobilization compound immobilized on a solid support. This immobilization product will be referred to in the following as the immobilization product of the invention and is used in the methods of the present invention.

In a preferred embodiment, the immobilization compound or immobilization product of the invention may further be labelled.

By "labeled" is meant that the respective substance is either directly or indirectly labeled with a molecule which provides a detection signal, e.g. radioisotope, fluorescent tag, chemiluminescent tag, a peptide or specific binding molecules. Specific binding molecules include pairs, such as biotin and streptavidin, digoxin and antidigoxin. The label can directly or indirectly provide a detectable signal. The tag can also be a peptide which can be used in an enzyme fragment complementation assay (e.g. beta-galactosidase enzyme fragment complementation; Zaman et al., 2006. Assay Drug Dev. Technol. 4(4):411-420).

Radioisotopes are commonly used in biological applications for the detection of a variety of biomolecules and have proven to be useful in binding assays. Several examples of probes have been designed to incorporate $^3$H (tritium) because it can replace hydrogen in a probe without altering its structure (Fenteany et al., 1995. Science 268:726-731).

Guidance for the selection and methods for the attachment of fluorescent tags (e.g. fluorescein, rhodamine, dansyl, NBD (nitrobenz-2-oxa-1,3-diazole), BODIPY (dipyrromethene boron difluoride), and cyanine (Cy)-dyes) to small molecule ligands are generally known in the art (Vedvik et al., 2004. Assay Drug Dev. Technol. 2(2): 193-203; Zhang et al., 2005. Analytical Biochemistry 343(1):76-83). The application of fluorescent probes (fluorophores) in assays for high throughput screening (HTS) of protein kinases was described (Zaman et al., 2003. Comb. Chem. High Throughput Screen 6(4): 313-320). The change of the fluorescent properties after binding of the fluorescent probe to the target kinase can be determined by measuring for example fluorescence polarization (Kashem et al., 2007. J. Biomol. Screening 12(1):70-83), fluorescence resonance energy transfer (FRET; Zhang et al., 2005. Analytical Biochemistry 343(1):76-83) or fluorescence lifetime (Moger et al., 2006. J. Biomol. Screening 11(7): 765-772).

As already discussed above, one possible use of the immobilization products of the invention is in the context of the identification of JAK. Therefore, the present invention also relates to such methods and uses.

In a first aspect of the methods of the invention, the invention therefore relates to a method for the identification of a JAK interacting compound, comprising the steps of a) providing a protein preparation containing JAK,
b) contacting the protein preparation with the immobilization product of the invention under conditions allowing the formation of a complex between JAK and the immobilization product,
c) incubating the complex with a given compound, and
d) determining whether the compound is able to separate JAK from the immobilization product.

In a second aspect of the methods of the invention, the present invention relates to a method for the identification of a JAK interacting compound, comprising the steps of a) providing a protein preparation containing JAK,
b) contacting the protein preparation with the immobilization product of the invention and with a given compound under conditions allowing the formation of a complex between JAK and the immobilization product, and
c) detecting the complex formed in step b).

In a third aspect of the methods of the invention, the invention provides a method for the identification of a JAK interacting compound, comprising the steps of:

a) providing two aliquots of a protein preparation containing JAK,
b) contacting one aliquot with the immobilization product of the invention under conditions allowing the formation of a complex between JAK and the immobilization product,
c) contacting the other aliquot with the immobilization product and with a given compound under conditions allowing the formation of the complex, and
d) determining the amount of the complex formed in steps b) and c).

In a fourth aspect of the methods of the invention, the invention relates to a method for the identification of a JAK interacting compound, comprising the steps of:

a) providing two aliquots comprising each at least one cell containing JAK,
b) incubating one aliquot with a given compound,
c) harvesting the cells of each aliquot,
d) lysing the cells in order to obtain protein preparations,
e) contacting the protein preparations with the immobilization product of the invention under conditions allowing the formation of a complex between JAK and the immobilization product, and
f) determining the amount of the complex formed in each aliquot in step e).

According to the present invention "JAK" comprises all members of the JAK family (e.g. JAK1, JAK2, JAK3, and TYK2).

The sequence of human JAK1 is given in FIG. 6. The human gene encoding JAK1 is located on chromosome 1p31.3.

The sequence of human JAK2 is given in FIG. 7. The human gene encoding JAK2 is located on chromosome 9p24.

The sequence of human JAK3 is given in FIG. 8 and the sequence of human TYK2 is given in FIG. 9. The JAK3 and TYK2 genes are clustered on chromosome 19p13.1 and 19p13.2, respectively.

According to the present invention, the expression "JAK" relates to both human and other proteins of this family. The expression especially includes functionally active derivatives thereof, or functionally active fragments thereof, or a homologues thereof, or variants encoded by a nucleic acid that hybridizes to the nucleic acid encoding said protein under low stringency conditions. Preferably, these low stringency conditions include hybridization in a buffer comprising 35% formamide, 5×SSC, 50 mM Tris-HCl (pH 7.5), 5 mM EDTA, 0.02% PVP, 0.02% BSA, 100 ug/ml denatured salmon sperm DNA, and 10% (wt/vol) dextran sulfate for 18-20 hours at 40° C., washing in a buffer consisting of 2×SSC, 25 mM Tris-HCl (pH 7.4), 5 mM EDTA, and 0.1% SDS for 1-5 hours at 55° C., and washing in a buffer consisting of 2×SSC, 25 mM Tris-HCl (pH 7.4) 5 mM EDTA, and 0.1% SDS for 1.5 hours at 60° C.

Moreover, according to the present invention, the expression "JAK" includes mutant forms of JAK kinases, preferably JAK2 mutant forms that are observed in myeloproliferative diseases (e.g. polycytemia vera, essential thrombocythemia and primary myelofibrosis) and JAK3 mutants found in acute megakaryoblastic leukemia (AMKL) patients. More preferred, these mutants are single amino acid mutations.

The single amino acid mutation V617F in JAK2 is one of the most frequently observed mutations (Levine et al., 2007. Nat. Rev. Cancer. 7(9): 673-683). This mutation is present in haematopoietic cells but not germline DNA in patients with myeloproliferative disorders demonstrating that JAK2V617F is a somatic mutation that is acquired in the haematopoietic compartment. The JAK2V617F mutation is located in the JH2 pseudo-kinase domain of the JAK2 protein.

Although most patients with PV carry the JAK2V617F mutant, some patients are negative for this allele. Analysis of JAK2V617F negative PV patients identified four novel somatic mutations in exon 12 of JAK2 (Scott et al., 2007. N. Engl. J. Med 356, 459-468). One mutant is a point mutation that results in the replacement of lysine for leucine at codon 539 (K539L). Three additional mutations were small deletions or insertions involving codons 538 to 543 (F537-K539delinsL, H538QK539L, and N542-E543del) (see FIG. 1 in Scott et al., 2007. N. Engl. J. Med 356, 459-468).

Therefore, in a preferred embodiment, the expression "JAK" also includes a JAK2 protein having a V617F mutation, a K539L mutation, and deletion mutations in exon 12.

Activating JAK3 mutations were observed in acute megakaryoblastic leukemia (AMKL) patients (Walters et al., 2006. Cancer Cell 10(1):65-75).

Therefore, in a preferred embodiment, the expression "JAK" also includes a JAK3 protein having a V722I or P132T mutation.

The compounds of the presence invention are a ligand for all isoforms of JAK (see above). However, throughout the invention, it is preferred that JAK means JAK2 or JAK3, especially the human isoforms thereof.

In some aspects of the invention, first a protein preparation containing JAK is provided. The methods of the present invention can be performed with any protein preparation as a starting material, as long as the JAK is solubilized in the preparation. Examples include a liquid mixture of several proteins, a cell lysate, a partial cell lysate which contains not all proteins present in the original cell or a combination of several cell lysates. The term "protein preparation" also includes dissolved purified protein.

The presence of JAK protein species in a protein preparation of interest can be detected on Western blots probed with antibodies that are specifically directed against JAK. In case that JAK is a specific isoform (e.g. JAK3), the presence of said isoform can be determined by an isoform-specific antibody. Such antibodies are known in the art (Zhu et al., 1998. J. Biol. Chem. 273(17):10682-9). Alternatively, also mass spectrometry (MS) could be used to detect JAK (see below).

Cell lysates or partial cell lysates can be obtained by isolating cell organelles (e.g. nucleus, mitochondria, ribosomes, golgi etc.) first and then preparing protein preparations derived from these organelles. Methods for the isolation of cell organelles are known in the art (Chapter 4.2 Purification of Organelles from Mammalian Cells in "Current Protocols in Protein Science", Editors: John. E. Coligan, Ben M. Dunn, Hidde L. Ploegh, David W. Speicher, Paul T. Wingfield; Wiley, ISBN: 0-471-14098-8).

In addition, protein preparations can be prepared by fractionation of cell extracts thereby enriching specific types of proteins such as cytoplasmic or membrane proteins (Chapter 4.3 Subcellular Fractionation of Tissue Culture Cells in "Current Protocols in Protein Science", Editors: John. E. Coligan, Ben M. Dunn, Hidde L. Ploegh, David W. Speicher, Paul T. Wingfield; Wiley, ISBN: 0-471-14098-8).

Furthermore protein preparations from body fluids can be used (e.g. blood, cerebrospinal fluid, peritoneal fluid and urine).

For example whole embryo lysates derived from defined development stages or adult stages of model organisms such as *C. elegans* can be used. In addition, whole organs such as heart dissected from mice can be the source of protein preparations. These organs can also be perfused in vitro in order to obtain a protein preparation.

Furthermore, the protein preparation may be a preparation containing JAK which has been recombinantly produced. Methods for the production of recombinant proteins in prokaryotic and eukaryotic cells are widely established (Chapter 5 Production of Recombinant Proteins in "Current Protocols in Protein Science", Editors: John. E. Coligan, Ben M. Dunn, Hidde L. Ploegh, David W. Speicher, Paul T. Wingfield; Wiley, 1995, ISBN: 0-471-14098-8).

In a preferred embodiment of the methods of the invention, the provision of a protein preparation includes the steps of harvesting at least one cell containing JAK and lysing the cell.

Suitable cells for this purpose are e.g. those cells or tissues were members of the JAK family are expressed. JAK1, JAK2 and TYK2 are expressed in most cells and tissues. JAK3 is preferentially expressed in cells of the hematopoietic system (e.g. monocytes and B-cells).

Therefore, in a preferred embodiment, cells isolated from peripheral blood represent a suitable biological material. Procedures for the preparation and culture of human lymphocytes and lymphocyte subpopulations obtained from peripheral blood (PBLs) are widely known (W. E Biddison, Chapter 2.2 "Preparation and culture of human lymphocytes" in Current Protocols in Cell Biology, 1998, John Wiley & Sons, Inc.). For example, density gradient centrifugation is a method for the separation of lymphocytes from other blood cell populations (e.g. erythrocytes and granulocytes). Human lymphocyte subpopulations can be isolated via their specific cell surface receptors which can be recognized by monoclonal antibodies. The physical separation method involves coupling of these antibody reagents to magnetic beads which allow the enrichment of cells that are bound by these antibodies (positive selection). The isolated lymphocyte cells can be further cultured and stimulated by adding cytokines to initiate receptor-mediated cell signalling and subsequently phosphorylation of STAT proteins (Schindler et al., 2007. 282(28): 20059-20063).

As an alternative to primary human cells cultured cell lines (e.g. MOLT-4 cells, Jurkat or Ramos cells) can be used.

In a preferred embodiment, the cell is part of a cell culture system and methods for the harvest of a cell out of a cell culture system are known in the art (literature supra).

The choice of the cell will mainly depend on the expression of JAK, since it has to be ensured that the protein is principally present in the cell of choice. In order to determine whether a given cell is a suitable starting system for the methods of the invention, methods like Westernblot, PCR-based nucleic acids detection methods, Northernblots and DNA-microarray methods ("DNA chips") might be suitable in order to determine whether a given protein of interest is present in the cell.

The choice of the cell may also be influenced by the purpose of the study. If the in vivo efficacy for a given drug needs to be analyzed then cells or tissues may be selected in which the desired therapeutic effect occurs (e.g. B-cells). By contrast, for the elucidation of protein targets mediating unwanted side effects the cell or tissue may be analysed in which the side effect is observed (e.g. cardiomyocytes, vascular smooth muscle or epithelium cells).

Furthermore, it is envisaged within the present invention that the cell containing JAK may be obtained from an organism, e.g. by biopsy. Corresponding methods are known in the art. For example, a biopsy is a diagnostic procedure used to obtain a small amount of tissue, which can then be examined microscopically or with biochemical methods. Biopsies are important to diagnose, classify and stage a disease, but also to evaluate and monitor drug treatment.

It is encompassed within the present invention that by the harvest of the at least one cell, the lysis is performed simultaneously. However, it is equally preferred that the cell is first harvested and then separately lysed.

Methods for the lysis of cells are known in the art (Karwa and Mitra: Sample preparation for the extraction, isolation, and purification of Nuclei Acids; chapter 8 in "Sample Preparation Techniques in Analytical Chemistry", Wiley 2003, Editor: Somenath Mitra, print ISBN: 0471328456; online ISBN: 0471457817). Lysis of different cell types and tissues can be achieved by homogenizers (e.g. Potter-homogenizer), ultrasonic disintegrators, enzymatic lysis, detergents (e.g. NP-40, Triton X-100, CHAPS, SDS), osmotic shock, repeated freezing and thawing, or a combination of these methods.

According to the methods of the invention, the protein preparation containing JAK is contacted with the immobilization product under conditions allowing the formation of a complex between JAK and the immobilization product of the invention.

In the present invention, the term "a complex between JAK and the immobilization product" denotes a complex where the immobilization product interacts with JAK, e.g. by covalent or, most preferred, by non-covalent binding.

The skilled person will know which conditions can be applied in order to enable the formation of said complex.

In the context of the present invention, the term "under conditions allowing the formation of the complex" includes all conditions under which such formation, preferably such binding is possible. This includes the possibility of having the solid support on an immobilized phase and pouring the lysate onto it. In another preferred embodiment, it is also included that the solid support is in a particulate form and mixed with the cell lysate.

In the context of non-covalent binding, the binding between the immobilization product and JAK is, e.g., via salt bridges, hydrogen bonds, hydrophobic interactions or a combination thereof.

In a preferred embodiment, the steps of the formation of said complex are performed under essentially physiological conditions. The physical state of proteins within cells is described in Petty, 1998 (Howard R. Petty[1], Chapter 1, Unit 1.5 in: Juan S. Bonifacino, Mary Dasso, Joe B. Harford, Jennifer Lippincott-Schwartz, and Kenneth M. Yamada (eds.) *Current Protocols in Cell Biology* Copyright © 2003 John Wiley & Sons, Inc. All rights reserved. DOI: 10.1002/0471143030.cb0101s00 Online Posting Date: May, 2001 Print Publication Date: October, 1998).

The contacting under essentially physiological conditions has the advantage that the interactions between the ligand, the cell preparation (i.e. the kinase to be characterized) and optionally the compound reflect as much as possible the natural conditions. "Essentially physiological conditions" are inter alia those conditions which are present in the original, unprocessed sample material. They include the physiological protein concentration, pH, salt concentration, buffer capacity and post-translational modifications of the proteins involved. The term "essentially physiological conditions" does not require conditions identical to those in the original living organism, wherefrom the sample is derived, but essentially cell-like conditions or conditions close to cellular conditions. The person skilled in the art will, of course, realize that certain constraints may arise due to the experimental set-up which will eventually lead to less cell-like conditions. For example, the eventually necessary disruption of cell walls or cell membranes when taking and processing a sample from a living organism may require conditions which are not identical to the physiological conditions found in the organism. Suitable variations of physiological conditions for practicing the methods of the invention will be apparent to those skilled in the art and are encompassed by the term "essentially physiological conditions" as used herein. In summary, it is to be understood that the term "essentially physiological conditions" relates to conditions close to physiological conditions, as e.g. found in natural cells, but does not necessarily require that these conditions are identical.

For example, "essentially physiological conditions" may comprise 50-200 mM NaCl or KCl, pH 6.5-8.5, 20-37° C., and 0.001-10 mM divalent cation (e.g. Mg++, Ca++,); more preferably about 150 m NaCl or KCl, pH7.2 to 7.6, 5 mM divalent cation and often include 0.01-1.0 percent non-specific protein (e.g. BSA). A non-ionic detergent (Tween, NP-40, Triton-X100) can often be present, usually at about 0.001 to 2%, typically 0.05-0.2% (volume/volume). For general guidance, the following buffered aqueous conditions may be applicable: 10-250 mM NaCl, 5-50 mM Tris HCl, pH5-8, with optional addition of divalent cation(s) and/or metal chelators and/or non-ionic detergents.

Preferably, "essentially physiological conditions" mean a pH of from 6.5 to 7.5, preferably from 7.0 to 7.5, and/or a buffer concentration of from 10 to 50 mM, preferably from 25 to 50 mM, and/or a concentration of monovalent salts (e.g. Na or K) of from 120 to 170 mM, preferably 150 mM. Divalent salts (e.g. Mg or Ca) may further be present at a concentration of from 1 to 5 mM, preferably 1 to 2 mM, wherein more preferably the buffer is selected from the group consisting of Tris-HCl or HEPES.

The skilled person will appreciate that between the individual steps of the methods of the invention, washing steps may be necessary. Such washing is part of the knowledge of the person skilled in the art. The washing serves to remove non-bound components of the cell lysate from the solid support. Nonspecific (e.g. simple ionic) binding interactions can be minimized by adding low levels of detergent or by moderate adjustments to salt concentrations in the wash buffer.

According to the identification methods of the invention, the read-out system is either the detection or determination of JAK (first aspect of the invention), the detection of the complex between JAK and the immobilization product (second aspect of the invention), or the determination of the amount of the complex between JAK and the immobilization product (second, third and fourth aspect of the invention).

In the method according to the first aspect of the invention, the detection or determination of the amount of separated JAK is preferably indicative for the fact that the compound is able to separate JAK from the immobilization product. This capacity indicates that the respective compound interacts, preferably binds to JAK, which is indicative for its therapeutic potential.

In one embodiment of the method according to the second aspect of the invention, the complex formed during the method of the invention is detected. The fact that such complex is formed preferably indicates that the compound does not completely inhibit the formation of the complex. On the other hand, if no complex is formed, the compound is presumably a strong interactor with JAK, which is indicative for its therapeutic potential.

According to the methods of the second, third and fourth aspect of the invention the amount of the complex formed during the method is determined. In general, the less complex in the presence of the respective compound is formed, the stronger the respective compound interacts with JAK, which is indicative for its therapeutic potential.

The detection of the complex formed according to the second aspect of the invention can be performed by using labeled antibodies directed against JAK and a suitable read-out system.

According to a preferred embodiment of the second aspect of the invention, the complex between JAK and the immobilization product is detected by determining its amount.

In the course of the second, third and fourth aspect of the invention, it is preferred that JAK is separated from the immobilization product in order to determine the amount of said complex.

According to invention, separating means every action which destroys the interactions between the immobilization compound and JAK. This includes in a preferred embodiment the elution of JAK from the immobilization compound.

The elution can be achieved by using non-specific reagents as described in detail below (ionic strength, pH value, detergents). In addition, it can be tested whether a compound of interest can specifically elute the JAK from the immobilization compound. Such JAK interacting compounds are described further in the following sections.

Such non-specific methods for destroying the interaction are principally known in the art and depend on the nature of the ligand enzyme interaction. Principally, change of ionic strength, the pH value, the temperature or incubation with detergents are suitable methods to dissociate the target enzymes from the immobilized ligand. The application of an elution buffer can dissociate binding partners by extremes of pH value (high or low pH; e.g. lowering pH by using 0.1 M citrate, pH2-3), change of ionic strength (e.g. high salt concentration using NaI, KI, $MgCl_2$, or KCl), polarity reducing agents which disrupt hydrophobic interactions (e.g. dioxane or ethylene glycol), or denaturing agents (chaotropic salts or detergents such as Sodium-docedyl-sulfate, SDS; Review: Subramanian A., 2002, Immunoaffinity chromatography).

In some cases, the solid support has preferably to be separated from the released material. The individual methods for this depend on the nature of the solid support and are known in the art. If the support material is contained within a column the released material can be collected as column flowthrough. In case the support material is mixed with the lysate components (so called batch procedure) an additional separation step such as gentle centrifugation may be necessary and the released material is collected as supernatant. Alternatively magnetic beads can be used as solid support so that the beads can be eliminated from the sample by using a magnetic device.

In step d) of the method according to the first aspect of the invention, it is determined if JAK has been separated from the immobilization product of the invention. This may include the detection of JAK or the determination of the amount JAK.

Consequently, at least in preferred embodiments of all identification methods of the invention, methods for the detection of separated JAK or for the determination of its amount are used. Such methods are known in the art and include physico-chemical methods such as protein sequencing (e.g. Edmann degradation), analysis by mass spectrometry methods or immunodetection methods employing antibodies directed against JAK.

Throughout the invention, if an antibody is used in order to detect JAK or in order to determine its amount (e.g. via ELISA), the skilled person will understand that, if a specific isoform of JAK is to be detected or if the amount of a specific isoform of JAK is to be determined, an isoform-specific antibody may be used. As indicated above, such antibodies are known in the art. Furthermore, the skilled person is aware of methods for producing the same.

Preferably, JAK is detected or the amount of JAK is determined by mass spectrometry or immunodetection methods.

The identification of proteins with mass spectrometric analysis (mass spectrometry) is known in the art (Shevchenko et al., 1996, Analytical Chemistry 68: 850-858; Mann et al., 2001, Analysis of proteins and proteomes by mass spectrometry, Annual Review of Biochemistry 70, 437-473) and is further illustrated in the example section.

Preferably, the mass spectrometry analysis is performed in a quantitative manner, for example by using iTRAQ technology (isobaric tags for relative and absolute quantification) or cICAT (cleavable isotope-coded affinity tags) (Wu et al., 2006. J. Proteome Res. 5, 651-658).

According to a further preferred embodiment of the present invention, the characterization by mass spectrometry (MS) is performed by the identification of proteotypic peptides of JAK. The idea is that JAK is digested with proteases and the resulting peptides are determined by MS. As a result, peptide frequencies for peptides from the same source protein differ by a great degree, the most frequently observed peptides that "typically" contribute to the identification of this protein being termed "proteotypic peptide". Therefore, a proteotypic peptide as used in the present invention is an experimentally well observable peptide that uniquely identifies a specific protein or protein isoform.

According to a preferred embodiment, the characterization is performed by comparing the proteotypic peptides obtained in the course of practicing the methods of the invention with known proteotypic peptides. Since, when using fragments prepared by protease digestion for the identification of a protein in MS, usually the same proteotypic peptides are observed for a given enzyme, it is possible to compare the proteotypic peptides obtained for a given sample with the proteotypic peptides already known for enzymes of a given class of enzymes and thereby identifying the enzyme being present in the sample.

As an alternative to mass spectrometry analysis, the eluted JAK (including coeluted binding partners or scaffold proteins), can be detected or its amount can be determined by using a specific antibody directed against JAK (or against an isoform of JAK, see above).

Furthermore, in another preferred embodiment, once the identity of the coeluted binding partner has been established by mass spectrometry analysis, each binding partner can be detected with specific antibodies directed against this protein.

Suitable antibody-based assays include but are not limited to Western blots, ELISA assays, sandwich ELISA assays and antibody arrays or a combination thereof. The establishment of such assays is known in the art (Chapter 11, Immunology, pages 11-1 to 11-30 in: Short Protocols in Molecular Biology. Fourth Edition, Edited by F. M. Ausubel et al., Wiley, New York, 1999).

These assays can not only be configured in a way to detect and quantify a JAK interacting protein of interest (e.g. a catalytic or regulatory subunit of a JAK complex), but also to analyse posttranslational modification patterns such as phosphorylation or ubiquitin modification.

Furthermore, the identification methods of the invention involve the use of compounds which are tested for their ability to be a JAK interacting compound.

Principally, according to the present invention, such a compound can be every molecule which is able to interact with JAK, eg. by inhibiting its binding to the immobilization product of the invention. Preferably, the compound has an effect on JAK, e.g. a stimulatory or inhibitory effect.

Preferably, said compound is selected from the group consisting of synthetic or naturally occurring chemical compounds or organic synthetic drugs, more preferably small molecule organic drugs or natural small molecule compounds. Preferably, said compound is identified starting from a library containing such compounds. Then, in the course of the present invention, such a library is screened.

Such small molecules are preferably not proteins or nucleic acids. Preferably, small molecules exhibit a molecular weight of less than 1000 Da, more preferred less than 750 Da, most preferred less than 500 Da.

A "library" according to the present invention relates to a (mostly large) collection of (numerous) different chemical entities that are provided in a sorted manner that enables both a fast functional analysis (screening) of the different individual entities, and at the same time provide for a rapid identification of the individual entities that form the library. Examples are collections of tubes or wells or spots on surfaces that contain chemical compounds that can be added into reactions with one or more defined potentially interacting partners in a high-throughput fashion. After the identification of a desired "positive" interaction of both partners, the respective compound can be rapidly identified due to the library construction. Libraries of synthetic and natural origins can either be purchased or designed by the skilled artisan.

Examples of the construction of libraries are provided in, for example, Breinbauer R, Manger M, Scheck M, Waldmann H. Natural product guided compound library development. Curr Med Chem. 2002 December; 9(23):2129-45, wherein natural products are described that are biologically validated starting points for the design of combinatorial libraries, as they have a proven record of biological relevance. This special role of natural products in medicinal chemistry and chemical biology can be interpreted in the light of new insights about the domain architecture of proteins gained by structural biology and bioinformatics. In order to fulfill the specific requirements of the individual binding pocket within a domain family it may be necessary to optimise the natural product structure by chemical variation. Solid-phase chemistry is said to become an efficient tool for this optimisation process, and recent advances in this field are highlighted in this review article. Other related references include Edwards P J, Morrell A I. Solid-phase compound library synthesis in drug design and development. Curr Opin Drug Discov Devel. 2002 July; 5(4):594-605.; Merlot C, Domine D, Church D J. Fragment analysis in small molecule discovery. Curr Opin Drug Discov Devel. 2002 May; 5(3):391-9. Review; Goodnow R A Jr. Current practices in generation of small molecule new leads. J Cell Biochem Suppl. 2001; Suppl 37:13-21; which describes that the current drug discovery processes in many pharmaceutical companies require large and growing collections of high quality lead structures for use in high throughput screening assays. Collections of small molecules with diverse structures and "drug-like" properties have, in the past, been acquired by several means: by archive of previous internal lead optimisation efforts, by purchase from compound vendors, and by union of separate collections following company mergers. Although high throughput/combinatorial chemistry is described as being an important component in the process of new lead generation, the selection of library designs for synthesis and the subsequent design of library members has evolved to a new level of challenge and importance. The potential benefits of screening multiple small molecule compound library designs against multiple biological targets offers substantial opportunity to discover new lead structures.

In a preferred embodiment of the second and third aspect of the invention, the JAK containing protein preparation is first incubated with the compound and then with the immobilization product. However, the simultaneous incubation of the compound and the immobilization product of the invention (coincubation) with the JAK containing protein preparation is equally preferred (competitive binding assay).

In case that the incubation with the compound is first, the JAK is preferably first incubated with the compound for 10 to 60 minutes, more preferred 30 to 45 minutes at a temperature of 4° C. to 37° C., more preferred 4° C. to 25° C., most preferred 4° C. Preferably compounds are used at concentrations ranging from 1 nM to 100 µM, preferably from 10 nM to 10 µM. The second step, contacting with the immobilized ligand, is preferably performed for 10 to 60 minutes at 4° C.

In case of simultaneous incubation, the JAK is preferably simultaneously incubated with the compound and the immobilization product of the invention for 30 to 120 minutes, more preferred 60 to 120 minutes at a temperature of 4° C. to 37° C., more preferred 4° C. to 25° C., most preferred 4° C. Preferably compounds are used at concentrations ranging from 1 nM to 100 µM, preferably from 10 nM to 10 µM.

Furthermore, steps a) to c) of the second aspect of the invention may be performed with several protein preparations in order to test different compounds. This embodiment is especially interesting in the context of medium or high throughput screenings (see below).

In a preferred embodiment of the method of the invention according to the third or fourth aspect, the amount of the complex formed in step c) is compared to the amount formed in step b).

In a preferred embodiment of the method of the invention according to the third or fourth aspect, a reduced amount of the complex formed in step c) in comparison to step b) indicates that JAK is a target of the compound. This results from the fact that in step c) of this method of the invention, the compound competes with the ligand for the binding of JAK. If less JAK is present in the aliquot incubated with the compound, this means preferably that the compound has competed with the inhibitor for the interaction with the enzyme and is, therefore, a direct target of the protein and vice versa.

Preferably, the identification methods of the invention are performed as a medium or high throughput screening.

The interaction compound identified according to the present invention may be further characterized by determining whether it has an effect on JAK, for example on its kinase activity (Changelian et al., 2003, Science 302(5646):875-888 and online supplement; Yang et al., 2007. Bioorg. Med. Chem. Letters 17(2): 326-331). Such assays are known in the art, also in a format that allows medium to high throughput screening (Fuchikami et al., 2002, J. Biomol. Screening 7, 441-450).

Briefly, JAK kinase activity can be measured using a recombinant GST-JAK fusion protein comprising the catalytic domain (JH1 catalytic domain). JAK kinase activity is measured by ELISA as follows: Plates are coated overnight with a random L-glutamic acid and tyrosine co-polymer (4:1; 100 µg/ml) as a substrate. The plates are washed and recombinant JAK JH1:GST protein (100 ng/well) with or without inhibitors is incubated at room temperature for 30 minutes. The a HPR-conjugated PY20 anti-phosphotyrosine antibody (ICN) is added and developed by TMB (3,3',5,5'-tetramethylbenzidine) (Changelian et al., 2003, Science 302(5646): 875-888 and online supplement).

For the determination of JAK protein kinase activity a fluorescence polarization assay with a suitable peptide substratecan be used. Briefly, a fluorescein-labeled peptide substrate may be incubated with JAK (e.g. JAK3), ATP and an anti-phosptyrosine antibody. As the reaction proceeds, the phosphorylated peptide binds to the anti-phosphotyrosine antibody, resulting in an increase in the polarization signal. Compounds that inhibit the kinase result in a low polarization signal.

The compounds identified according to the present invention may further be optimized (lead optimisation). This subsequent optimisation of such compounds is often accelerated because of the structure-activity relationship (SAR) information encoded in these lead generation libraries. Lead optimisation is often facilitated due to the ready applicability of high-throughput chemistry (HTC) methods for follow-up synthesis.

An example for lead optimization of JAK3 inhibitors was reported (Chen et al., 2006. Bioorg. Med. Chem. Letters 16(21): 5633-5638).

The invention further relates to a method for the preparation of a pharmaceutical composition comprising the steps of
 a) identifying a JAK interacting compound as described above, and
 b) formulating the interacting compound to a pharmaceutical composition.

Therefore, the invention provides a method for the preparation of pharmaceutical compositions, which may be administered to a subject in an effective amount. In a preferred aspect, the therapeutic is substantially purified. The subject to be treated is preferably an animal including, but not limited to animals such as cows, pigs, horses, chickens, cats, dogs, etc., and is preferably a mammal, and most preferably human. In a specific embodiment, a non-human mammal is the subject.

The compounds identified according to the invention are useful for the prevention or treatment of diseases where JAK plays a role (for example JAK2 inhibitors for myeloproliferative diseases such as polycytemia vera and JAK3 inhibitors for immunosuppression to prevent organ transplant rejection). Consequently, the present invention also relates to the use of a compound identified by the methods of the invention for the preparation of a medicament for the treatment of one or more of the above mentioned diseases. Furthermore, the present invention relates to a pharmaceutical composition comprising said compound.

In general, the pharmaceutical compositions of the present invention comprise a therapeutically effective amount of a therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

In a preferred embodiment, the composition is formulated, in accordance with routine procedures, as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water or saline for injection can be provided so that the ingredients may be mixed prior to administration.

The therapeutics of the invention can be formulated as neutral or salt forms. Pharmaceutically acceptable salts include those formed with free carboxyl groups such as those derived from hydrochloric, phosphoric, acetic, oxalic, tartaric acids, etc., those formed with free amine groups such as those derived from isopropylamine, triethylamine, 2-ethylamino ethanol, histidine, procaine, etc., and those derived from sodium, potassium, ammonium, calcium, and ferric hydroxides, etc.

The amount of the therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems. In general, suppositories may contain active ingredient in the range of 0.5% to 10% by weight; oral formulations preferably contain 10% to 95% active ingredient.

Various delivery systems are known and can be used to administer a therapeutic of the invention, e.g., encapsulation in liposomes, microparticles, and microcapsules: use of recombinant cells capable of expressing the therapeutic, use of receptor-mediated endocytosis (e.g., Wu and Wu, 1987, J. Biol. Chem. 262:4429-4432); construction of a therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion, by bolus injection, by absorption through epithelial or mucocutaneous linings (e.g., oral, rectal and intestinal mucosa, etc.), and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment. This may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, the therapeutic can be delivered in a vesicle, in particular a liposome (Langer, 1990, Science 249:1527-1533).

In yet another embodiment, the therapeutic can be delivered via a controlled release system. In one embodiment, a pump may be used (Langer, supra). In yet another embodiment, a controlled release system can be placed in proximity of the therapeutic target, i.e., the brain, thus usually requiring only a fraction of the systemic dose.

The invention further relates to a method for the purification of JAK, comprising the steps of
a) providing a protein preparation containing JAK,
b) contacting the protein preparation with the immobilization product of the invention under conditions allowing the formation of a complex between JAK and the immobilization product, and
c) separating JAK from the immobilization product.

As mentioned above, it has been surprisingly found that the compound of the invention and therefore also the immobilization product of the invention is a ligand which recognizes JAK. This enables efficient purification methods for JAK.

With respect to JAK, the protein preparation containing JAK, the conditions for contacting with the immobilization product of the invention, the immobilization product of the invention, the complex between JAK and the immobilization product of the invention, the separation of JAK from the immobilization product of the invention, and the detection of JAK or the determination of its amount, the embodiments as defined above for the identification methods of the invention also apply to the purification method of the invention.

In a preferred embodiment, the method of purification further comprises the step of purifying a specific isoform or specific isoforms of JAK, preferably the step of purifying JAK2 and/or JAK3.

Preferably, said purification is performed using an isoform specific antibody as explained above, more preferably a JAK2 specific antibody and/or a JAK3 specific antibody.

In a preferred embodiment, the purification method of the invention further comprises after step c) the identification of proteins being capable of binding to JAK. This is especially interesting when the formation of the complex is performed under essentially physiological conditions, because it is then possible to preserve the natural condition of the enzyme which includes the existence of binding partners, enzyme subunits or post-translational modifications, which can then be identified with the help of mass spectrometry (MS).

Consequently, in a preferred embodiment, the purification method of the invention further comprises after step c) the determination whether the JAK is further posttranslationally modified, e.g. by ubiquitin modification.

The binding proteins or the posttranslational modifications can be determined as explained above for the detection of JAK or the determination of the amount of JAK. Preferably, said methods include mass spectrometry of immunodetection methods as described above.

The invention further relates to a method for determining the presence of JAK in a sample, comprising the steps of:
a) providing a protein preparation expected to contain JAK,
b) contacting the protein preparation with the immobilization product of the invention under conditions allowing the formation of a complex between JAK and the immobilization product, and
c) detecting whether JAK has formed a complex with the immobilization product.

In a preferred embodiment of the invention, said detecting in step c) is performed by separating JAK from the immobilization product and further identification of JAK.

Said identification may be performed by mass spectrometry or immunodetection methods as described above.

Preferably, also in the context of this method of the invention JAK is JAK2 or JAK3.

According to an especially preferred embodiment of this method of the invention, the JAK contains at least one mutation, i.e. is a mutant form of JAK, preferably one of those mutant forms disclosed above. More preferably, the JAK is a JAK mutant form observed in myeloproliferative diseases (e.g. polycytemia vera, essential thrombocythemia and primary myelofibrosis) or in acute megakaryoblastic leukemia (AMKL) as described above.

With respect to JAK, the protein preparation containing JAK, the conditions for contacting with the immobilization product of the invention, the immobilization product of the invention, the complex between JAK and the immobilization product of the invention, the separation of JAK from the immobilization product of the invention, and the detection of JAK or the determination of its amount, the embodiments as defined above for the identification methods of the invention also apply to the purification method of the invention.

The invention further relates to the use of compound or the immobilization product of the invention for the identification of JAK interacting compounds and for the purification of JAK. The embodiments as defined above also apply to the uses of the invention.

The invention further relates to a kit comprising the compound or the immobilization product of the invention. Such a kit is especially useful for performing the methods of the invention. Further components of the kit may be antibodies for the detection of JAK proteins, for example antibodies specific for JAK2 and/or JAK3 and antibodies directed at phosphorylation sites of JAK proteins. Such antibodies and their use are known in the art and they are commercially available (Zhu et al., 1998. J. Biol. Chem. 273(17):10682-9; Scott et al., 2007. N. Engl. J. Med. 356(5):459-68; Neilson et al., 2007. Molecular Endocrinology 21(9):2218-2232). Furthermore, the kit may contain further auxiliary components like buffers, means for the detection of antibodies, positive controls, etc. Such components are known in the art.

The invention is further illustrated by the following figures and examples, which are not considered as being limiting for the scope of protection conferred by the claims of the present application.

SHORT DESCRIPTION OF THE FIGURES

FIG. 1: Synthesis of 5-(4-((2,3-dimethyl-2H-indazol-6-yl)(methyl)amino)pyrimidin-2-ylamino)-2-methylbenzenesulfonamide (IX). The compound was synthesized as described in example 1.

Figure 2:
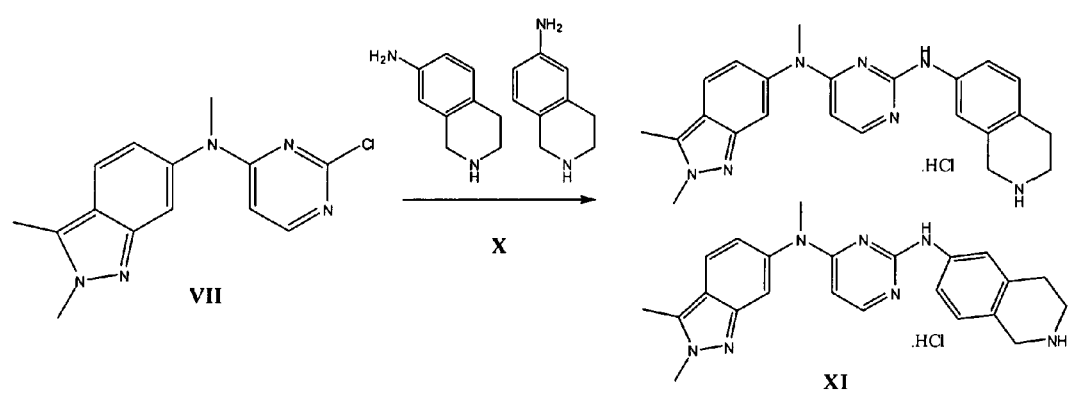

FIG. 2: Synthesis of N4-(2,3-dimethyl-2H-indazol-6-yl)-N4-methyl-N2-(1,2,3,4-tetrahydroisoquinolin-7-yl)pyrimidine-2,4-diamine and N4-(2,3-dimethyl-2H-indazol-6-yl)-N4-methyl-N2-(1,2,3,4-tetrahydroisoquinolin-6-yl)pyrimidine-2,4-diamine (XI). The compounds were synthesized as described in example 1.

Figure 3:
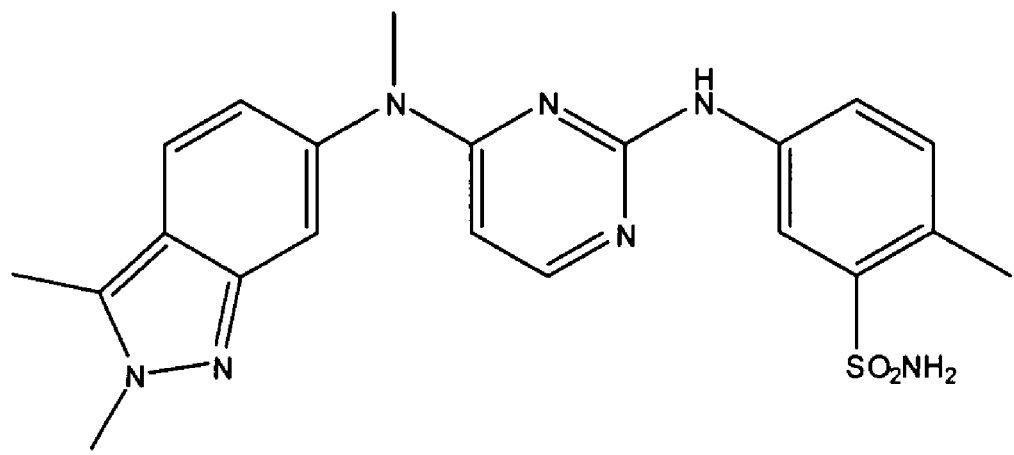

FIG. 3: Structure of 5-(4-((2,3-dimethyl-2H-indazol-6-yl)(methyl)amino)pyrimidin-2-ylamino)-2-methylbenzenesulfonamide.

Figure 4:
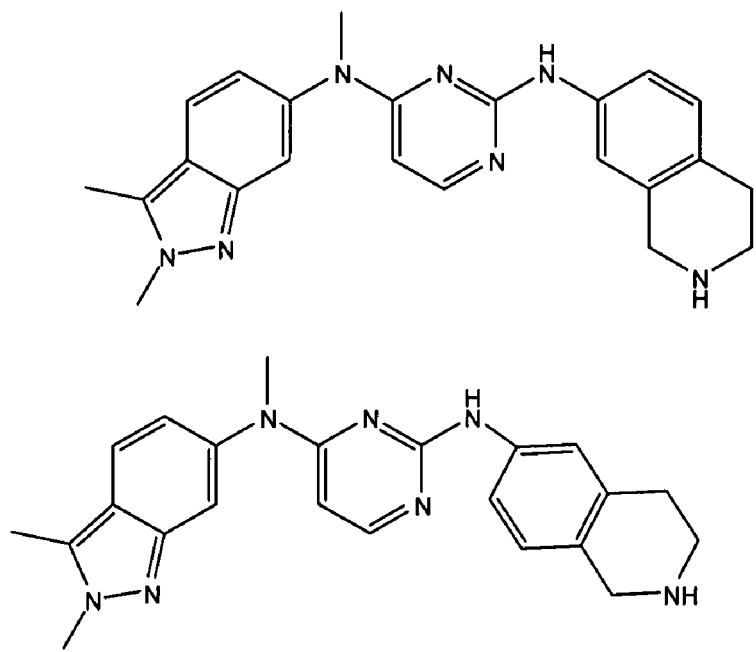

FIG. 4: Structures of N4-(2,3-dimethyl-2H-indazol-6-yl)-N4-methyl-N2-(1,2,3,4-tetrahydroisoquinolin-7-yl)pyrimidine-2,4-diamine and N4-(2,3-dimethyl-2H-indazol-6-yl)-N4-methyl-N2-(1,2,3,4-tetrahydroisoquinolin-6-yl)pyrimidine-2,4-diamine.

Figure 5:
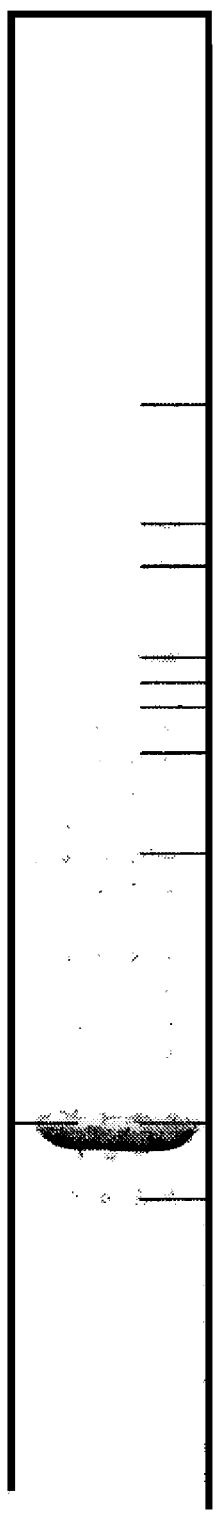

FIG. 5: Drug pulldown experiment with the immobilized compounds (isomer pair shown in FIG. 4) for mass spectrometry analysis of captured proteins. A protein gel after staining with Coomassie brilliant blue is shown. The drug pulldown experiment was performed as described in example 2 with a 1:1 mixture of Jurkat and Ramos cell lysates containing 50 mg of protein. Proteins bound to the affinity matrix were eluted with SDS sample buffer and separated by SDS-polyacrylamide gel electrophoresis. The indicated gel areas were cut out as gel slices, proteins were treated with trypsin and subjected to analysis by mass spectrometry.

FIG. 6: Amino acid sequence of human JAK1 (IPI00011633.2). Peptides identified by mass spectrometry after a drug pulldown experiment are shown in bold type and underlined.

FIG. 7: Amino acid sequence of human JAK2 (IPI000031016.1). Peptides identified by mass spectrometry after a drug pulldown experiment are shown in bold type and underlined.

FIG. 8: Amino acid sequence of human JAK3 (IPI00002773.4). Peptides identified by mass spectrometry after a drug pulldown experiment are shown in bold type and underlined.

FIG. 9: Amino acid sequence of human Tyk2 (IPI00022353.4). Peptides identified by mass spectrometry after a drug pulldown experiment are shown in bold type and underlined.

Figure 10:
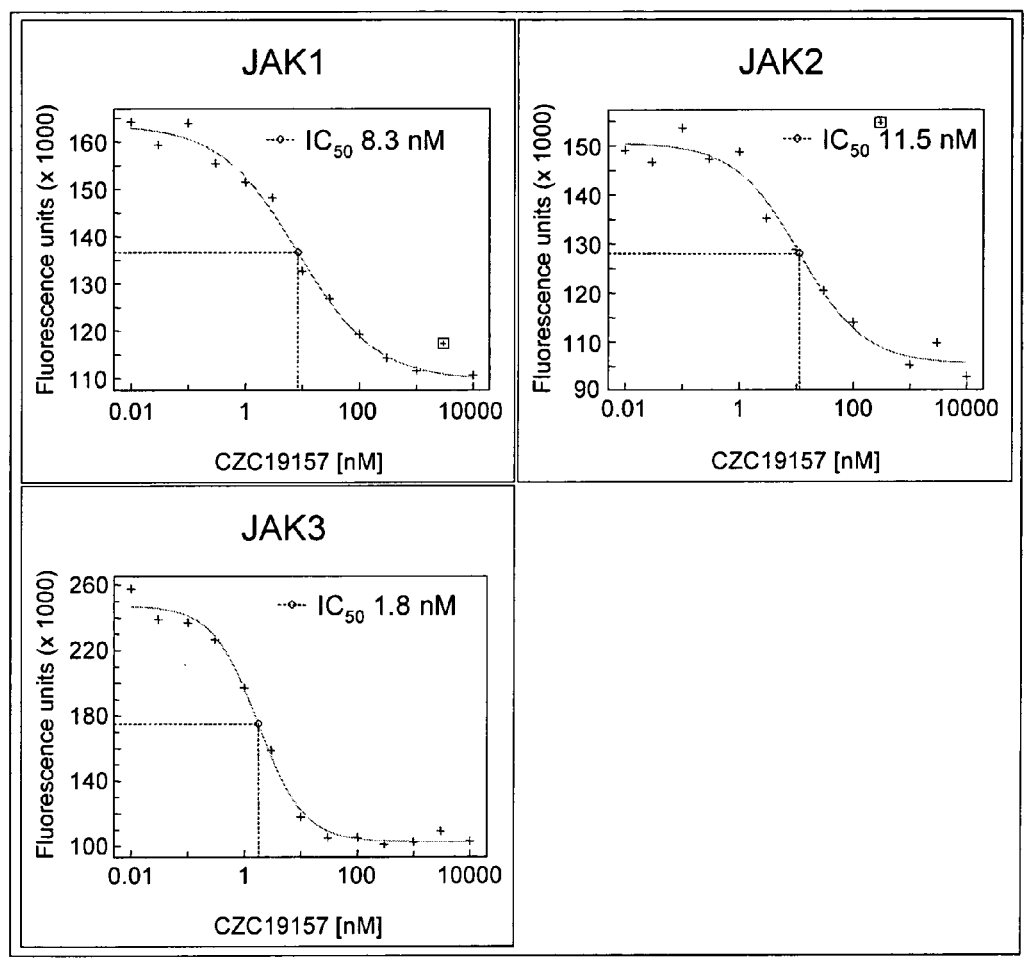

FIG. 10: Competition binding assay with reference compound 1 in Jurkat cell lysate and detection of JAK1, JAK2 and JAK3 with specific antibodies.

The experiment was performed as described in example 3. The test compound (or DMSO as solvent control) was added at the indicated concentrations to Jurkat cell lysate and incubated for 30 minutes at 4° C. Then the affinity matrix (an immobilization product of the invention comprising the isomer pair shown in FIG. 4) was added and the mix was incubated for another 90 minutes at 4° C. After washing, captured proteins were eluted with SDS-containing sample buffer. A manual pintool was utilized for spotting of eluted samples onto nitrocellulose glass slides. The slide was first incubated with an anti-JAK antibody in Odyssey buffer containing 0.2% Tween 20 (overnight incubation at 4° C.; for JAK1: 1:50 dilution, rabbit polyclonal antibody, Cell Signaling Technology, cat. No. 3332; for JAK2: 1:50 dilution, rabbit monoclonal antibody, Cell Signaling Technology, cat. No. 3229; for JAK3: 50 dilution, rabbit polyclonal antibody, Cell Signaling Technology, cat. No. 3775). A secondary detection antibody labeled with a fluorescent dye was used with the Odyssey infrared imaging system (IRDye 800 nm anti-rabbit antibody (Licor) diluted 1:10000 in Odyssey buffer with 0.2% Tween 20, 0.02% SDS, one hour incubation at room temperature). For the compound CZC19157 $IC_{50}$ values of 8.3, 11.5 and 1.3 nM were observed for JAK1, JAK2 and JAK3, respectively.

EXAMPLES

Example 1

Preparation of the Affinity Matrix

This example describes the synthesis of compounds and methods for their immobilization on a solid support yielding the affinity matrix used in the following examples for the capturing of JAK family kinases (JAK1, JAK2, JAK3 and Tyk2) from cell lysates.

Synthetic Scheme 1 (FIG. 1)

Synthesis of 5-(4-((2,3-dimethyl-2H-indazol-6-yl)(methyl)amino)pyrimidin-2-ylamino)-2-methylbenzenesulfonamide (IX)

Preparation 2-ethyl-5-nitroaniline (II)

2-ethylaniline (12.1 g, 99.8 mmol, 1 equiv) was dissolved in concentrated sulphuric acid (50 ml) and cooled down to 0° C. Fuming nitric acid (9.3 g, 147.6 mmol, 1.5 equiv) was then added slowly keeping the temperature below 5° C. The reaction was left warm up to room temperature and stirred overnight. The reaction mixture was poured onto ice-water (250 ml) and neutralised with sodium hydroxide 6M. The solid was filtered off and dried in an oven to remove as much water as possible. The red solid was then taken up in petrol (250 ml×4) and decanted over filter paper to crystallise out the desired compound as yellow solid. (2.7 g, 17%). 1H NMR spectra were recorded at ambient temperature using a Bruker Advance DRX (400 MHz) spectrometer, both with a triple resonance 5 mm probe. Chemical shifts are expressed in ppm relative to tetramethylsilane.

¹H NMR (CDCl₃, 400 MHz) δ=7.51 (d, J=8 Hz, 1H), 7.43 (s, 1H), 7.10 (d, J=8 Hz, 1H), 3.7 (br s, 2H), 2.5 (q, J=7 Hz, 2H), 1.21 (t, J=7 Hz, 3H).

Preparation of 3-methyl-6-nitro-2H-indazole (III)

2-ethyl-5-nitroaniline (1.03 g, 6.2 mmol, 1 equiv) was dissolved in glacial acetic acid (30 ml) at room temperature under nitrogen. Tert-butylnitrite (0.9 ml, 7.5 ml, 1.2 equiv) in glacial acetic acid (16 ml) was added drop wise over 20 min. The reaction was stirred for 30 min and the acid was removed under vacuum to give an orange solid. The solid was taken up in ethyl acetate (50 ml) and washed with saturated sodium bicarbonate solution (3×50 ml). The organics layers were dried over magnesium sulphate and concentrated to yield the desired compounds as of a brown solid (0.85 g, 77.4%).
¹H NMR (CDCl₃, 400 MHz) δ=9.67, (br s, 1H), 8.36 (d, J=2 Hz, 1H), 7.95 (dd, J=2 Hz, J=9 Hz, 1H), 7.73 (d, J=9 Hz, 1H), 2.70 (s, 3H).

Preparation 2,3-dimethyl-6-nitro-2H-indazole (IV)

3-methyl-6-nitro-2H-indazole (0.85 g, 5 mmol, 1 equiv) was dissolved in DMSO (4 ml) and treated with sulphuric acid (0.26 ml, 5 mmol, 1 equiv) to yield a thick slurry that was treated with dimethylsulfate (1.36 ml, 14 mmol, 2.8 equiv). The reaction mixture was heated to 50° C. under nitrogen for 72 hrs. The reaction mixture was cooled down to room temperature and treated with a saturated solution of sodium bicarbonate (10 ml). The reaction mixture was extracted with DCM (2×20 ml). The organic layers were washed with water (20 ml). Propanol was added and the organic layers were evaporated under vacuum to yield a solid which was filtered and washed with heptane (5 ml). The desired compound was collected as a brown solid (0.48 g, 50%).
¹H NMR (d6-DMSO, 400 MHz) δ=8.54 (d, J=2 Hz, 1H), 7.94 (d, J=9 Hz, 1H), 7.76 (dd, J=2 Hz, J=9 Hz, 1H), 4.17 (s, 3H), 2.69 (s, 3H).

Preparation of 2,3-dimethyl-2H-indazol-6-amine (V)

2,3-dimethyl-6-nitro-2H-indazole (0.48 g, 2.5 mmol, 1 equiv) was dissolved in 2-methoxyethylether (4.3 ml) with heating then cooled down to 0° C. Tin chloride (1.6 g, 7.1 mmol, 2.8 equiv) was added under nitrogen. Concentrated HCl (3.2 ml) was added dropwise keeping the temperature below 5° C. When all the HCl was added, the reaction was allowed to warm up to room temperature and stirred for 45 min. Ether (14 ml) was added and a precipitate was collected too yield the desired product as an hydrochloride salt (0.35 g, 86.8%).
¹H NMR (d6-DMSO, 400 MHz) δ=7.67 (d, J=8 Hz, 1H), 7.12 (s, 1H), 6.79 (d, J=8 Hz, 1H), 4.56 (br s, 2H), 2.50 (s, 3H).

Preparation of N-(2-chloropyrimidin-4-yl)-2,3-dimethyl-2H-indazol-6-amine (VI)

2,3-dimethyl-2H-imidazole-6-amine HCl (0.58 g, 3 mmol) was stirred with sodium bicarbonate (1.02 g, 12 mmol, 4 equiv) in THF (3 ml) and ethanol (12 ml). 2,4-dichloropyrimidine (1.37 g, 9 mmol, 3 equiv) was added and the reaction mixture was stirred at 77° C. under nitrogen for 4 hrs. The reaction was cooled down to room temperature and filtered. The grey solid was washed with ethyl acetate to yield the desired compound (0.74 g, 90%).

¹H NMR (d6-DMSO, 400 MHz) δ=10.6 (br s, 1H, 8.15 (d, J=8 Hz, 1H), 8.05 (br s, 1H), 7.6 (d, J=9 Hz, 1H), 7.15 (d, J=9 Hz, 1H), 7.0 (d, J=8 Hz, 1H), 4.0 (s, 3H), 2.52 (s, 3H).

Preparation of N-(2-chloropyrimidin-4-yl)-N,2,3-trimethyl-2H-indazol-6-amine (VII)

N-(2-chloropyrimidin-4-yl)-2,3-dimethyl-2H-indazol-6-amine (2.21 g; 8 mmol, 1 equiv) was dissolved in DMF (11 ml) and cesium carbonate (7.9 g; 24.2 mmol, 3 equiv) was added. The reaction mixture was stirred for 30 min under nitrogen. Iodomethane (0.8 ml, 13 mmol, 1.6 equiv) was added and the reaction mixture was stirred at room temperature for 2 hrs. The reaction mixture was poured in ice cold water and stirred for 30 minutes. The resulting precipitate was collected by filtration to yield the desired compound (0.84 g, 37%).
¹H NMR (MeOD, 400 MHz) δ=7.75 (d, J=7 Hz, 1H), 7.71 (d, J=7 Hz, 1H), 7.35 (d, J=2 Hz, 1H), 6.8 (dd, J=2 Hz, J=9 Hz, 1H), 6.14 (d, J=6 Hz, 1H), 4.01 (s, 3H), 3.4 (s, 3H), 2.56 (s, 3H).

Preparation of 5-amino-2-methylbenzenesulfonimide (VIII)

Chlorosulfonic acid (36.0 ml, 546 mmol, 6.5 equiv) was added very slowly to 4-methyl acetanilide (12.5 g, 83.9 mmol). The reaction was very vigorous and the temperature controlled below 20° C. by an ice-water bath. The resulting thick grey paste was heated to 75° C. for 45 min to give a green solution. The solution was poured dropwise in ice-water (350 ml). The resulting off-grey solid was filtered. Ammonium hydroxide (45 ml) was added carefully. 50 ml of sulfuric acid 20% was then added (pH 2) to give a lavender suspension. The suspension was stirred at 5° C. for 10 min then filtered. The solid was washed with water (2×100 ml) and air dried for 20 min. The solid was then refluxed with HCl 6N (50 ml) for 2 hrs. When there was no solid left, the reaction was cooled down to room temperature and diluted with water (50 ml). The mixture was basified to pH 8 with sodium carbonate. A pale grey solid was filtered (5 g). The rest of the aqueous was evaporated to dryness and 50 ml of water was added. A grey/lavender solid was filtered. This was washed with water (3×10 ml) and air dried (3.5 g). Both crops were cautiously washed with methanol (3×10 ml) to yield the desired product (4.5 g, 28.8%).
¹H NMR (d6-DMSO, 400 MHz) δ=7.15 (br s, 3H), 6.96 (s, 1H), 6.62 (s, 1H), 5.27 (s, 2H), 2.38 (s, 3H).

Preparation of 5-(44(2,3-dimethyl-2H-indazol-6-yl) (methyl)amino)pyrimidin-2-ylamino)-2-methylbenzenesulfonamide (IX)

To a solution of N-(2-chloropyrimidin-4-yl)-N,2,3-trimethyl-2H-indazol-6-amine (55 mg; 0.2 mmol, 1 equiv) and 5-amino-2-methylbenzenesulfonimide (37 mg; 0.2 mmol, 1 equiv) in isopropanol (2 ml) was added 1 drop of concentrated HCl. The reaction mixture was refluxed overnight. The reaction mixture was cooled down to room temperature and diluted with diethyl ether (2 ml). The precipitate was filtered and washed with diethyl ether. The solid was then boiled in ethanol and filtered to yield the desired product as a white solid hydrochloride salt (0.070 g, 77%).
¹H NMR (400 MHz, d6-DMSO; 11.5 (br s, 1H), 8.42 (br s, 1H), 7.95 (d, J=8.0 Hz, 1H), 7.85 (br s, 1H), 7.62 (s, 1H), 7.45

(s, 2H), 6.95 (d, J=8.0 Hz, 1H), 5.87 (br s, 1H, 4.03 (s, 3H), 3.75 (s, 3H), 2.65 (s, 3H), 2.57 (s, 3H).

Synthetic Scheme 2 (FIG. 2)

Synthesis of N4-(2,3-dimethyl-2H-indazol-6-yl)-N4-methyl-N2-(1,2,3,4-tetrahydroisoquinolin-7-yl)pyrimidine-2,4-diamine and N4-(2,3-dimethyl-2H-indazol-6-yl)-N4-methyl-N2-(1,2,3,4-tetrahydroisoquinolin-6-yl)pyrimidine-2,4-diamine (XI)

Preparation of a mixture of 7-nitro-1,2,3,4-tetrahydroisoquinoline and 6-nitro-1,2,3,4-tetrahydroisoquinoline 1,2,3,4-tetrahydroisoquinolin (10.0 g, 75.1 mmol, 1 equiv) was dissolved in 40 ml of concentrated sulfuric acid (exothermic reaction) and potassium nitrate (8.4 g, 83.0 mmol, 1.1 equiv) was added in portions over 1 hour whilst stirring at 0° C. The reaction mixture was then warmed up to room temperature and stirred for 2 hrs. The reaction was poured in ice-water (100 ml) and basified to pH 10 with ammonia solution (100 ml). The mixture was then extracted with chloroform (2×250 ml). The combined extracts were washed with brine, dried over magnesium sulfate and concentrated to give a dark red oil. The residue was purified by column chromatography using DCM/MeOH/NH$_4$OH:95/5/0.5 to give the title mixture of isomers as a solid (7 g, 52%).

$^1$H NMR (CDCl$_3$, 400 MHz) δ=7.99 (m, 1H), 7.92 (s, 1H), 7.28 (m, 1H), 7.26 (m, 1H), 4.1 (s, 2H), 3.17 (m, 2H), 2.9 (m, 2H).

Preparation of a mixture of 1,2,3,4-tetrahydroisoquinolin-7-amine and 1,2,3,4-tetrahydroisoquinolin-6-amine (X)

The mixture of 7-nitro-1,2,3,4-tetrahydroisoquinoline and 6-nitro-1,2,3,4-tetrahydroisoquinoline (1.0 g, 5.6 mmol, 1 equiv) was dissolved in a mixture of aqueous ammonium chloride [(2.4 g, 44.8 mmol, 8 equiv) in 6 ml of water] and ethanol (4 ml). Iron powder (1.3 g, 23.3 mmol, 4 equiv) was added and the reaction mixture was stirred at 60° C. for 24 hrs. The mixture was cooled down to room temperature and then filtered through Celite. The filter cake was washed with ethanol (50 ml). The orange solution was filtered again to remove any inorganics, concentrated in vacuum and azeotroped with toluene. The residue was stirred in ethanol (50 ml) at 40° C. and filtered. The filtrate was concentrated to give the title mixture as a yellow solid (0.85 g, 100%).

$^1$H NMR (MeOD, 400 MHz) δ=6.95 (m, 1H), 6.66 (m, 1H), 6.63 (m, 1H), 4.2 (m, 2H), 3.4 (m, 2H), 3.0 (m, 2H).

Preparation of a mixture of N4-(2,3-dimethyl-2H-indazol-6-yl)-N4-methyl-N-2-(1,2,3,4-tetrahydroisoquinolin-7-yl)pyrimidine-2,4-diamine and N4-(2,3-dimethyl-2H-indazol-6-yl)-N4-methyl-N2-(1,2,3,4-tetrahydroisoquinolin-6-yl)pyrimidine-2,4-diamine (XI)

To a solution of N-(2-chloropyrimidin-4-yl)-N,2,3-trimethyl-2H-indazol-6-amine (0.58 g, 2 mmol, 1 equiv) and a mixture of 1,2,3,4-tetrahydroisoquinolin-7-amine and 1,2,3,4-tetrahydroisoquinolin-6-amine (0.3 g; 2 mmol, 1 equiv) in isopropanol (17 ml) was added 12 drops of concentrated HCl. The reaction mixture was refluxed overnight, then cooled down to room temperature and diluted with diethyl ether (18 ml). The precipitate was filtered and washed with diethyl ether. The resulting solid was purified by column chromatography using DCM/MeOH:95/5 as eluent to give a white solid. After trituration with petrol then DCM, the title mixture of isomers was filtered as an hydrochloride salt (0.060 g, 7.5% yield).

$^1$H NMR (d6-DMSO, 400 MHz) δ=9.04 (m, 1H), 7.79 (m, 1H), 7.69 (d, 1H, J=9 Hz, 1H), 7.51 (m, 1H), 7.36 (m, 2H), 6.90 (d, J=10.0 Hz, 1H), 6.82 (d, J=9.0 Hz, 1H), 5.91 (m, 1H), 4.0 (s, 3H), 3.66 (s, 1H), 3.4 (s, 3H), 3.11 (m. 2H), 3.0 (m, 2H), 2.66 (m, 2H), 2.57 (m, 3H).

TABLE 1

| Abbreviations used | |
|---|---|
| br | broad |
| CDCl3 | deuterochloroform |
| d | doublet |
| dd | doublet of doublets |
| DMSO | dimethyl sulphoxide |
| MH4OH | Ammonium hydroxyde |
| g | gram |
| HCl | Hydrochloric acid |
| HOBT | N-Hydroxybenzotriazole |
| m | multiplet |
| mg | milligram |
| ml | millilitre |
| mmol | millimole |
| M | molar |
| MHz | megahertz |
| DMF | Dimethylformamide |
| Hz | Hertz |
| equiv | Equivalent |
| DCM | Dichloromethane |
| THF | Tetrahydrofuran |
| NMR | nuclear magnetic resonance |
| q | quartet |
| s | singlet |
| t | triplet |

Immobilization on Beads (Affinity Matrix)

NHS-activated Sepharose 4 Fast Flow (Amersham Biosciences, 17-0906-01) was equilibrated with anhydrous DMSO (Dimethylsulfoxid, Fluka, 41648, H20<=0.005%). 1 ml of settled beads was placed in a 15 ml Falcon tube, compound stock solution (mixture of two isomers as shown in FIG. 4; usually 100 mM in DMF or DMSO) was added (final concentration 0.2-2 μmol/ml beads) as well as 15 μl of triethylamine (Sigma, T-0886, 99% pure). Beads were incubated at room temperature in darkness on an end-over-end shaker (Roto Shake Genie, Scientific Industries Inc.) for 16-20 hours. Coupling efficiency is determined by HPLC. Non-reacted NHS-groups were blocked by incubation with aminoethanol at room temperature on the end-over-end shaker over night. Beads were washed with 10 ml of DMSO and were stored in isopropanol at −20° C. These beads were used as the affinity matrix in example 2 and 3. Control beads (no ligand immobilized) were generated by blocking the NHS-groups by incubation with aminoethanol as described above.

Example 2

Drug Pulldown of JAK1, JAK2, JAK3 and Tyk2 using Immobilized Compounds

This example demonstrates the use of the immobilized compounds (isomer pair shown in FIG. 4) for the capturing and identification of the JAK1, JAK2, JAK3 and Tyk2 proteins from mixed Jurkat and Ramos cell lysate. To this end, a mixture of lysates of Jurkat and Ramos cells was contacted with the affinity matrix described in example 1. Proteins binding to the immobilized compounds were identified by mass spectrometry (MS) analysis. Further experimental protocols can be found in WO2006/134056.

For the identification of proteins by mass spectrometry analysis the proteins captured by the affinity matrix were eluted in SDS sample buffer and subsequently separated by SDS-Polyacrylamide gel electrophoresis (FIG. 5). Suitable gel bands were cut out and subjected to in-gel proteolytic digestion with trypsin and analyzed by LC-MS/MS mass spectrometry. The identification of JAK1, JAK2, JAK3 and Tyk2 derived peptides by mass spectrometry is documented and the peptide sequence coverage of the JAK1, JAK2, JAK3 and Tyk2 sequences is shown in FIGS. 6, 7, 8, and 9.

1. Cell Culture

Jurkat cells (ATCC number TIB-152) and Ramos cells (ATCC number CRL-1596) were either obtained from an external supplier (CIL SA, Mons, Belgium) or grown in one litre Spinner flasks (Integra Biosciences, #182101) in suspension in RPMI 1640 medium (Invitrogen, #21875-034) supplemented with 10% Fetal Bovine Serum (Invitrogen, #10270-106) at a density between $0.2 \times 10^6$ and $1.0 \times 10^6$ cells/ml. Cells were harvested by centrifugation, washed once with 1×PBS buffer (Invitrogen, #14190-094) and cell pellets were frozen in liquid nitrogen and subsequently stored at −80° C.

2. Preparation of Cell Lysates

Cells were homogenized in a Potter S homogenizer in lysis buffer: 50 mM Tris-HCl, 0.8% NP40, 5% glycerol, 150 mM NaCl, 1.5 mM $MgCl_2$, 25 mM NaF, 1 mM sodium vanadate, 1 mM DTT, pH 7.5. One complete EDTA-free tablet (protease inhibitor cocktail, Roche Diagnostics, 1 873 580) per 25 ml buffer was added. The material was dounced 20 times using a mechanized POTTER S, transferred to 50 ml falcon tubes, incubated for 30 minutes on ice and spun down for 10 minutes at 20,000×g at 4° C. (10,000 rpm in Sorvall SLA600, precooled). The supernatant was transferred to an ultracentrifuge (UZ)-polycarbonate tube (Beckmann, 355654) and spun for 1 hour at 160.000×g at 4° C. (42.000 rpm in Ti50.2, precooled). The supernatant was transferred again to a fresh 50 ml falcon tube, the protein concentration was determined by a Bradford assay (BioRad) and samples containing 50 mg of protein per aliquot were prepared. The samples were immediately used for experiments or frozen in liquid nitrogen and stored frozen at −80° C. This procedure was applied for the preparation of Ramos and Jurkat cell lysates.

3. Ligand Pull-Down Experiment

Sepharose-beads with the immobilized ligand (100 µl beads per pull-down experiment) were equilibrated in lysis buffer and incubated with a cell lysate sample containing 50 mg of protein on an end-over-end shaker (Roto Shake Genie, Scientific Industries Inc.) for 2 hours at 4° C. Beads were collected, transferred to Mobicol-columns (MoBiTech 10055) and washed with 10 ml lysis buffer containing 0.4% NP40 detergent, followed by 5 ml lysis buffer with 0.2% detergent. To elute the bound protein, 60 µl 2×SDS sample buffer was added, the column was heated for 30 minutes at 50° C. and the eluate was transferred to a microfuge tube by centrifugation. Proteins were then alkylated with 108 mM iodoacetamid. Proteins were then separated by SDS-Polyacrylamide electrophoresis (SDS-PAGE).

4. Protein Identification by Mass Spectrometry 4.1 Protein Digestion Prior to Mass Spectrometric Analysis Gel-separated proteins were reduced and digested in gel essentially following the procedure described by Shevchenko et al., 1996, Anal. Chem. 68:850-858. Briefly, gel-separated proteins were excised from the gel using a clean scalpel, reduced using 10 mM DTT (in 5 mM ammonium bicarbonate, 54° C., 45 minutes) at room temperature in the dark. The reduced proteins were digested in gel with porcine trypsin (Promega) at a protease concentration of 12.5 ng/p1 in 5 mM ammonium bicarbonate. Digestion was allowed to proceed for 4 hours at 37° C. and the reaction was subsequently stopped using 5 µl 5% formic acid.

4.2 Sample Preparation Prior to Analysis by Mass Spectrometry

Gel plugs were extracted twice with 20 µl 1% TFA and pooled with acidified digest supernatants. Samples were dried in a vacuum centrifuge and resuspended in 10 µl 0.1% formic acid.

4.3. Mass Spectrometric Data Acquisition

Peptide samples were injected into a nano LC system (CapLC, Waters or Ultimate, Dionex) which was directly coupled either to a quadrupole TOF (QTOF2, QTOF Ultima, QTOF Micro, Micromass) or ion trap (LCQ Deca XP) mass spectrometer. Peptides were separated on the LC system using a gradient of aqueous and organic solvents (see below). Solvent A was 5% acetonitrile in 0.5% formic acid and solvent B was 70% acetonitrile in 0.5% formic acid.

TABLE 2

Peptides eluting off the LC system were partially sequenced within the mass spectrometer

| Time (min) | % solvent A | % solvent B |
|---|---|---|
| 0 | 95 | 5 |
| 5.33 | 92 | 8 |
| 35 | 50 | 50 |
| 36 | 20 | 80 |
| 40 | 20 | 80 |
| 41 | 95 | 5 |
| 50 | 95 | 5 |

4.4. Protein Identification

The peptide mass and fragmentation data generated in the LC-MS/MS experiments were used to query fasta formatted protein and nucleotide sequence databases maintained and updated regularly at the NCBI (for the NCBInr, dbEST and the human and mouse genomes) and European Bioinformatics Institute (EBI, for the human, mouse, *D. melanogaster* and *C. elegans* proteome databases). Proteins were identified by correlating the measured peptide mass and fragmentation data with the same data computed from the entries in the database using the software tool Mascot (Matrix Science; Perkins et al., 1999. Probability-based protein identification by searching sequence databases using mass spectrometry data. Electrophoresis 20, 3551-3567). Search criteria varied depending on which mass spectrometer was used for the analysis.

Example 3

Assay for the Identification of JAK1, JAK2 and JAK3 Interacting Compounds

This example demonstrates a competitive binding assay in which test compounds are added directly into a cell lysate. Various concentrations of test compounds were added to lysate samples and allowed to bind to the proteins contained in the lysate sample. Then the affinity matrix with the immobilized compounds (isomer pair shown in FIG. 4) was added in order to capture proteins not bound to the test compound. After the incubation time the beads with captured proteins were separated from the lysate. Bound proteins were then eluted and the presence of JAK1, JAK2 or JAK3 was detected and quantified using a specific antibodies and the Odyssey infrared detection system. Further experimental protocols can be found in WO2006/134056. Dose response curves for reference compound 1 were generated with $IC_{50}$ values of 8.3, 11.5 and 1.3 nM for JAK1, JAK2 and JAK3, respectively (FIG. 10).

Washing of Affinity Matrix

The affinity matrix as described in example 1 (0.3 ml of dry volume) was washed two times with 15 ml of 1×DP buffer, then washed with 15 ml of 1×DP buffer containing 0.4% NP40 and finally resuspended in 0.3 ml of 1×DP buffer containing 0.4% NP40 (20% beads slurry).

Preparation of Test Compounds

Stock solutions of test compounds were prepared in DMSO corresponding to a 50-fold higher concentration compared to the final desired test concentration (e.g. a 0.5 mM stock solution was prepared for a final test concentration of 10 µM). This dilution scheme resulted in a final DMSO concentration of 2%. For control experiments (no test compound) a buffer containing 2% DMSO was used. Reference compound 1: racemate of JAK3 inhibitor CP-690,550 (Changelian et al., 2003. Science 302, 875-878; WO 201/042246).

Dilution of Cell Lysate

Cell lysates were prepared as described in example 2. For a typical experiment one lysate aliquot containing 50 mg of protein was thawed in a 37° C. water bath and then kept at 4° C. To the lysate one volume of 1×DP buffer containing protease inhibitor (1 tablet of protease inhibitor dissolved in 25 ml of 1×DP buffer or 25 ml of 1×DP buffer containing 0.4% NP40; EDTA-free tablet protease inhibitor cocktail from Roche Applied Sciences, catalogue number 41647) was added so that a final NP40 concentration of 0.4% was obtained. The lysate was further diluted by adding 1×DP buffer containing 0.4% NP40 and proteinase inhibitors so that a final protein concentration of 5 mg/ml was achieved.

Incubation of Cell Lysate with Test Compound and Affinity Matrix, Elution and Spotting onto Nitrocellulose Slides 5 µl of compound reference compound 1 (diluted in DMSO) was added to 150 µl of Jurkat lysate (containing 5 mg of protein) in a 96 well filter plate. The mixture was incubated for 30 minutes at 750 rpm on a Thermomixer in the cold room (4° C.). Then 50 µl of the affinity matrix with the immobilized compounds (isomer pair shown in FIG. 4) (20% slurry) were added and incubated for 90 minutes at 4° C. After separation of the beads from the lysate by centrifugation, bound proteins were eluted with 20 µl of 2× concentrated sample buffer containing 50 mM DTT.

Eluates were spotted with a pintool (Manual Glass Slide Arrayer Replicator, Eight-Pin, V &P Scientific, Inc.) onto nitrocellulose film slides (21 mm×50 mm; Grace Bio-Labs, #305170).

Detection and Quantification of Eluted JAK1, JAK2 and JAK3

Immunodetection was performed according to standard procedures and the JAK1, JAK2, JAK3 proteins were detected and quantified by using specific anti-JAK antibodies diluted 1:50 in Odyssey buffer (LI-COR Biosciences (Lincoln, Nebr., USA) containing 0.2% Tween-20 (overnight incubation at 4° C.; for JAK1: rabbit polyclonal antibody, Cell Signaling Technology, cat. No. 3332; for JAK2: rabbit monoclonal antibody, Cell Signaling Technology, cat. No. 3229; for JAK3: rabbit polyclonal antibody, Cell Signaling Technology, cat. No. 3775). Fluorescently labeled secondary antibody (used at a dilution of 1:10000) and the Odyssey Infrared Imaging system (both from LI-COR Biosciences) were utilized according to instructions provided by the manufacturer. Dose response curves were computed with the XL fit program (XLfit4 Excel Add-In Version 4.2.0 Build 13; IDBS, Guilford, UK).

The invention claimed is:

1. An immobilization compound of formula (I)

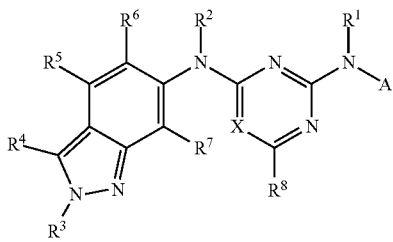

or a salt thereof, wherein

X is N or C(R⁹);

R¹, R², R³ are independently selected from the group consisting of H or $C_{1-4}$ alkyl;

R⁴, R⁵, R⁶, R⁷, R⁸, R⁹ are independently selected from the group consisting of H; halogen; $C_{1-4}$ alkyl; $OC_{1-4}$ alkyl; OH, wherein $C_{1-4}$ alkyl is optionally substituted with one or more R¹⁰;

R¹⁰ is halogen, OH or $C_{1-4}$ alkyl; and

A is

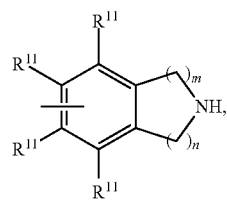

wherein each R¹¹ is independently selected from the group consisting of H; halogen;

$C_{1-4}$ alkyl; $OC_{1-4}$ alkyl; OH, wherein $C_{1-4}$ alkyl is optionally substituted with one or more R¹⁰;

n is 0, 1 or 2; and m is 1 or 2.

2. The immobilization compound of claim 1, selected from the group consisting of

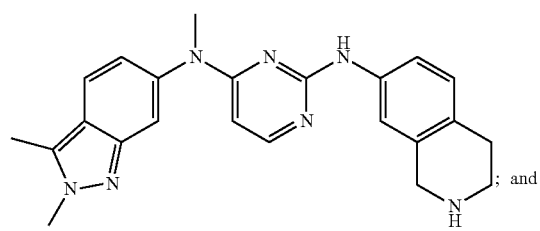
; and

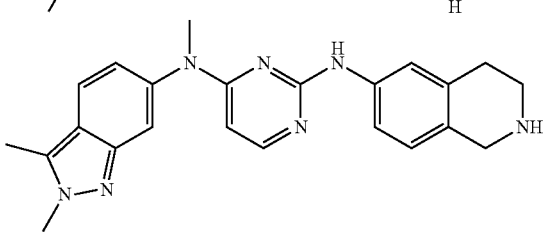

3. A method for the preparation of an immobilization product, comprising immobilizing at least one immobilization compound according to claim 1 on a solid support.

4. The method of claim 3, wherein the solid support is selected from the group consisting of agarose, modified agarose, sepharose beads, latex, cellulose, and ferro- or ferrimagnetic particles.

5. The method of claim 3, wherein the immobilization product results from a covalent direct or linker mediated attachment of the immobilization compound to the solid support,.

6. The method of claim 3, wherein said immobilization occurs via the ring nitrogen atom of the residue A in formula (I).

7. An immobilization product, comprising the immobilization compound of claim 1 immobilized on a solid support.

8. A method for the identification of a JAK interacting compound, comprising the steps of
    a) providing a protein preparation containing JAK,
    b) contacting the protein preparation with the immobilization product of claim 7 under conditions allowing the formation of a complex between JAK and the immobilization product,
    c) incubating the complex with a given compound, and
    d) determining whether the compound is able to separate JAK from the immobilization product.

9. A method for the identification of a JAK interacting compound, comprising the steps of
    a) providing a protein preparation containing JAK,
    b) contacting the protein preparation with the immobilization product of claim 7 and with a given compound under conditions allowing the formation of a complex between JAK and the immobilization product, and
    c) detecting the complex formed in step b).

10. A method for the identification of a JAK interacting compound, comprising the steps of:
    a) providing two aliquots of a protein preparation containing JAK,
    b) contacting one aliquot with the immobilization product of claim 7 under conditions allowing the formation of a complex between JAK and the immobilization product,
    c) contacting the other aliquot with the immobilization product and with a given compound under conditions allowing the formation of the complex, and
    d) determining the amount of the complex formed in steps b) and c).

11. The method of claim 10, wherein a reduced amount of the complex formed in the aliquot incubated with the compound in comparison to the aliquot not incubated with the compound indicates that JAK interacts with the compound.

12. The method of claim 10, wherein the amount of the complex is determined by separating JAK from the immobilization product and subsequent detection of separated JAK or subsequent determination of the amount of separated JAK.

13. The method of claim 12, wherein JAK is detected or the amount of JAK is determined by mass spectrometry or immunodetection methods.

14. The method of claim 10, performed as a medium or high throughput screening.

15. The method of claim 10, wherein said given compound is selected from the group consisting of synthetic compounds, or organic synthetic drugs, and natural small molecule compounds.

16. The method of claim 10, wherein the given compound is a JAK inhibitor.

17. The method of claim 10, wherein the JAK is JAK2 or JAK3.

18. A method for the identification of a JAK interacting compound, comprising the steps of:
   a) providing two aliquots comprising each at least one cell containing JAK,
   b) incubating one aliquot with a given compound,
   c) harvesting the cells of each aliquot,
   d) lysing the cells in order to obtain protein preparations,
   e) contacting the protein preparations with the immobilization product of claim 7 under conditions allowing the formation of a complex between JAK and the immobilization product, and
   f) determining the amount of the complex formed in each aliquot in step e).

19. A method for the purification of JAK, comprising the steps of
   a) providing a protein preparation containing JAK,
   b) contacting the protein preparation with the immobilization product of claim 7 under conditions allowing the formation of a complex between JAK and the immobilization product, and
   c) separating JAK from the immobilization product.

20. A method for determining the presence of JAK in a sample, comprising the steps of:
   a) providing a protein preparation expected to contain JAK,
   b) contacting the protein preparation with the immobilization product of claim 8 under conditions allowing the formation of a complex between JAK and the immobilization product, and
   c) detecting whether JAK has formed a complex with the immobilization product.

21. A kit comprising the immobilization compound according to any of claim 1 or 2 or the immobilization product according to claim 7 and one or more further auxiliary components.

* * * * *

SEQUENCE LISTING

```
<160> NUMBER OF SEQ ID NOS: 50

<210> SEQ ID NO 1
<211> LENGTH: 1154
<212> TYPE: PRT
<213> ORGANISM: Homo Sapiens

<400> SEQUENCE: 1

Met Gln Tyr Leu Asn Ile Lys Glu Asp Cys Asn Ala Met Ala Phe Cys
1               5                   10                  15

Ala Lys Met Arg Ser Ser Lys Lys Thr Glu Val Asn Leu Glu Ala Pro
            20                  25                  30

Glu Pro Gly Val Glu Val Ile Phe Tyr Leu Ser Asp Arg Glu Pro Leu
        35                  40                  45

Arg Leu Gly Ser Gly Glu Tyr Thr Ala Glu Glu Leu Cys Ile Arg Ala
    50                  55                  60

Ala Gln Ala Cys Arg Ile Ser Pro Leu Cys His Asn Leu Phe Ala Leu
65                  70                  75                  80

Tyr Asp Glu Asn Thr Lys Leu Trp Tyr Ala Pro Asn Arg Thr Ile Thr
                85                  90                  95

Val Asp Asp Lys Met Ser Leu Arg Leu His Tyr Arg Met Arg Phe Tyr
            100                 105                 110

Phe Thr Asn Trp His Gly Thr Asn Asp Asn Glu Gln Ser Val Trp Arg
        115                 120                 125
```

```
His Ser Pro Lys Lys Gln Lys Asn Gly Tyr Glu Lys Lys Ile Pro
    130                 135                 140

Asp Ala Thr Pro Leu Leu Asp Ala Ser Ser Leu Glu Tyr Leu Phe Ala
145                 150                 155                 160

Gln Gly Gln Tyr Asp Leu Val Lys Cys Leu Ala Pro Ile Arg Asp Pro
                165                 170                 175

Lys Thr Glu Gln Asp Gly His Asp Ile Glu Asn Glu Cys Leu Gly Met
                180                 185                 190

Ala Val Leu Ala Ile Ser His Tyr Ala Met Met Lys Lys Met Gln Leu
            195                 200                 205

Pro Glu Leu Pro Lys Asp Ile Ser Tyr Lys Arg Tyr Ile Pro Glu Thr
210                 215                 220

Leu Asn Lys Ser Ile Arg Gln Arg Asn Leu Leu Thr Arg Met Arg Ile
225                 230                 235                 240

Asn Asn Val Phe Lys Asp Phe Leu Lys Glu Phe Asn Asn Lys Thr Ile
                245                 250                 255

Cys Asp Ser Ser Val Ser Thr His Asp Leu Lys Val Lys Tyr Leu Ala
                260                 265                 270

Thr Leu Glu Thr Leu Thr Lys His Tyr Gly Ala Glu Ile Phe Glu Thr
            275                 280                 285

Ser Met Leu Leu Ile Ser Ser Glu Asn Glu Met Asn Trp Phe His Ser
290                 295                 300

Asn Asp Gly Gly Asn Val Leu Tyr Tyr Glu Val Met Val Thr Gly Asn
305                 310                 315                 320

Leu Gly Ile Gln Trp Arg His Lys Pro Asn Val Val Ser Val Glu Lys
                325                 330                 335

Glu Lys Asn Lys Leu Lys Arg Lys Lys Leu Glu Asn Lys His Lys Lys
                340                 345                 350

Asp Glu Glu Lys Asn Lys Ile Arg Glu Glu Trp Asn Asn Phe Ser Tyr
            355                 360                 365

Phe Pro Glu Ile Thr His Ile Val Ile Lys Glu Ser Val Val Ser Ile
370                 375                 380

Asn Lys Gln Asp Asn Lys Lys Met Glu Leu Lys Leu Ser Ser His Glu
385                 390                 395                 400

Glu Ala Leu Ser Phe Val Ser Leu Val Asp Gly Tyr Phe Arg Leu Thr
                405                 410                 415

Ala Asp Ala His His Tyr Leu Cys Thr Asp Val Ala Pro Pro Leu Ile
                420                 425                 430

Val His Asn Ile Gln Asn Gly Cys His Gly Pro Ile Cys Thr Glu Tyr
            435                 440                 445

Ala Ile Asn Lys Leu Arg Gln Glu Gly Ser Glu Gly Met Tyr Val
450                 455                 460

Leu Arg Trp Ser Cys Thr Asp Phe Asp Asn Ile Leu Met Thr Val Thr
465                 470                 475                 480

Cys Phe Glu Lys Ser Glu Gln Val Gln Gly Ala Gln Lys Gln Phe Lys
                485                 490                 495

Asn Phe Gln Ile Glu Val Gln Lys Gly Arg Tyr Ser Leu His Gly Ser
            500                 505                 510

Asp Arg Ser Phe Pro Ser Leu Gly Asp Leu Met Ser His Leu Lys Lys
            515                 520                 525

Gln Ile Leu Arg Thr Asp Asn Ile Ser Phe Met Leu Lys Arg Cys Cys
    530                 535                 540

Gln Pro Lys Pro Arg Glu Ile Ser Asn Leu Leu Val Ala Thr Lys Lys
```

```
            545                 550                 555                 560
        Ala Gln Glu Trp Gln Pro Val Tyr Pro Met Ser Gln Leu Ser Phe Asp
                        565                 570                 575

Arg Ile Leu Lys Lys Asp Leu Val Gln Gly Glu His Leu Gly Arg Gly
                        580                 585                 590

Thr Arg Thr His Ile Tyr Ser Gly Thr Leu Met Asp Tyr Lys Asp Asp
                        595                 600                 605

Glu Gly Thr Ser Glu Glu Lys Lys Ile Lys Val Ile Leu Lys Val Leu
                        610                 615                 620

Asp Pro Ser His Arg Asp Ile Ser Leu Ala Phe Phe Glu Ala Ala Ser
        625                 630                 635                 640

Met Met Arg Gln Val Ser His Lys His Ile Val Tyr Leu Tyr Gly Val
                        645                 650                 655

Cys Val Arg Asp Val Glu Asn Ile Met Val Glu Glu Phe Val Glu Gly
                        660                 665                 670

Gly Pro Leu Asp Leu Phe Met His Arg Lys Ser Asp Val Leu Thr Thr
                        675                 680                 685

Pro Trp Lys Phe Lys Val Ala Lys Gln Leu Ala Ser Ala Leu Ser Tyr
                        690                 695                 700

Leu Glu Asp Lys Asp Leu Val His Gly Asn Val Cys Thr Lys Asn Leu
        705                 710                 715                 720

Leu Leu Ala Arg Glu Gly Ile Asp Ser Glu Cys Gly Pro Phe Ile Lys
                        725                 730                 735

Leu Ser Asp Pro Gly Ile Pro Ile Thr Val Leu Ser Arg Gln Glu Cys
                        740                 745                 750

Ile Glu Arg Ile Pro Trp Ile Ala Pro Glu Cys Val Glu Asp Ser Lys
                        755                 760                 765

Asn Leu Ser Val Ala Ala Asp Lys Trp Ser Phe Gly Thr Thr Leu Trp
                        770                 775                 780

Glu Ile Cys Tyr Asn Gly Glu Ile Pro Leu Lys Asp Lys Thr Leu Ile
        785                 790                 795                 800

Glu Lys Glu Arg Phe Tyr Glu Ser Arg Cys Arg Pro Val Thr Pro Ser
                        805                 810                 815

Cys Lys Glu Leu Ala Asp Leu Met Thr Arg Cys Met Asn Tyr Asp Pro
                        820                 825                 830

Asn Gln Arg Pro Phe Phe Arg Ala Ile Met Arg Asp Ile Asn Lys Leu
                        835                 840                 845

Glu Glu Gln Asn Pro Asp Ile Val Ser Glu Lys Lys Pro Ala Thr Glu
        850                 855                 860

Val Asp Pro Thr His Phe Glu Lys Arg Phe Leu Lys Arg Ile Arg Asp
        865                 870                 875                 880

Leu Gly Glu Gly His Phe Gly Lys Val Glu Leu Cys Arg Tyr Asp Pro
                        885                 890                 895

Glu Gly Asp Asn Thr Gly Glu Gln Val Ala Val Lys Ser Leu Lys Pro
                        900                 905                 910

Glu Ser Gly Gly Asn His Ile Ala Asp Leu Lys Lys Glu Ile Glu Ile
                        915                 920                 925

Leu Arg Asn Leu Tyr His Glu Asn Ile Val Lys Tyr Lys Gly Ile Cys
                        930                 935                 940

Thr Glu Asp Gly Gly Asn Gly Ile Lys Leu Ile Met Glu Phe Leu Pro
        945                 950                 955                 960

Ser Gly Ser Leu Lys Glu Tyr Leu Pro Lys Asn Lys Asn Lys Ile Asn
                        965                 970                 975
```

| | | | | | | | | | | | |
|---|---|---|---|---|---|---|---|---|---|---|---|
|Leu|Lys|Gln|Gln|Leu|Lys|Tyr|Ala|Val|Gln|Ile|Cys|Lys|Gly|Met|Asp|
| | |980| | | |985| | | |990| |

Tyr Leu Gly Ser Arg Gln Tyr Val His Arg Asp Leu Ala Ala Arg Asn
              995                1000                 1005

Val Leu Val Glu Ser Glu His Gln Val Lys Ile Gly Asp Phe Gly
    1010                1015                1020

Leu Thr Lys Ala Ile Glu Thr Asp Lys Glu Tyr Tyr Thr Val Lys
    1025                1030                1035

Asp Asp Arg Asp Ser Pro Val Phe Trp Tyr Ala Pro Glu Cys Leu
    1040                1045                1050

Met Gln Ser Lys Phe Tyr Ile Ala Ser Asp Val Trp Ser Phe Gly
    1055                1060                1065

Val Thr Leu His Glu Leu Leu Thr Tyr Cys Asp Ser Asp Ser Ser
    1070                1075                1080

Pro Met Ala Leu Phe Leu Lys Met Ile Gly Pro Thr His Gly Gln
    1085                1090                1095

Met Thr Val Thr Arg Leu Val Asn Thr Leu Lys Glu Gly Lys Arg
    1100                1105                1110

Leu Pro Cys Pro Pro Asn Cys Pro Asp Glu Val Tyr Gln Leu Met
    1115                1120                1125

Arg Lys Cys Trp Glu Phe Gln Pro Ser Asn Arg Thr Ser Phe Gln
    1130                1135                1140

Asn Leu Ile Glu Gly Phe Glu Ala Leu Leu Lys
    1145                1150

<210> SEQ ID NO 2
<211> LENGTH: 1132
<212> TYPE: PRT
<213> ORGANISM: Homo sapiens

<400> SEQUENCE: 2

Met Gly Met Ala Cys Leu Thr Met Thr Glu Met Glu Gly Thr Ser Thr
1               5                   10                  15

Ser Ser Ile Tyr Gln Asn Gly Asp Ile Ser Gly Asn Ala Asn Ser Met
            20                  25                  30

Lys Gln Ile Asp Pro Val Leu Gln Val Tyr Leu Tyr His Ser Leu Gly
        35                  40                  45

Lys Ser Glu Ala Asp Tyr Leu Thr Phe Pro Ser Gly Glu Tyr Val Ala
    50                  55                  60

Glu Glu Ile Cys Ile Ala Ala Ser Lys Ala Cys Gly Ile Thr Pro Val
65                  70                  75                  80

Tyr His Asn Met Phe Ala Leu Met Ser Glu Thr Glu Arg Ile Trp Tyr
                85                  90                  95

Pro Pro Asn His Val Phe His Ile Asp Glu Ser Thr Arg His Asn Val
            100                 105                 110

Leu Tyr Arg Ile Arg Phe Tyr Phe Pro Arg Trp Tyr Cys Ser Gly Ser
        115                 120                 125

Asn Arg Ala Tyr Arg His Gly Ile Ser Arg Gly Ala Glu Ala Pro Leu
    130                 135                 140

Leu Asp Asp Phe Val Met Ser Tyr Leu Phe Ala Gln Trp Arg His Asp
145                 150                 155                 160

Phe Val His Gly Trp Ile Lys Val Pro Val Thr His Glu Thr Gln Glu
                165                 170                 175

Glu Cys Leu Gly Met Ala Val Leu Asp Met Met Arg Ile Ala Lys Glu
            180                 185                 190

-continued

```
Asn Asp Gln Thr Pro Leu Ala Ile Tyr Asn Ser Ile Ser Tyr Lys Thr
    195                 200                 205
Phe Leu Pro Lys Cys Ile Arg Ala Lys Ile Gln Asp Tyr His Ile Leu
210                 215                 220
Thr Arg Lys Arg Ile Arg Tyr Arg Phe Arg Arg Phe Ile Gln Gln Phe
225                 230                 235                 240
Ser Gln Cys Lys Ala Thr Ala Arg Asn Leu Lys Leu Lys Tyr Leu Ile
                245                 250                 255
Asn Leu Glu Thr Leu Gln Ser Ala Phe Tyr Thr Glu Lys Phe Glu Val
            260                 265                 270
Lys Glu Pro Gly Ser Gly Pro Ser Gly Glu Glu Ile Phe Ala Thr Ile
        275                 280                 285
Ile Ile Thr Gly Asn Gly Gly Ile Gln Trp Ser Arg Gly Lys His Lys
    290                 295                 300
Glu Ser Glu Thr Leu Thr Glu Gln Asp Leu Gln Leu Tyr Cys Asp Phe
305                 310                 315                 320
Pro Asn Ile Ile Asp Val Ser Ile Lys Gln Ala Asn Gln Glu Gly Ser
                325                 330                 335
Asn Glu Ser Arg Val Val Thr Ile His Lys Gln Asp Gly Lys Asn Leu
            340                 345                 350
Glu Ile Glu Leu Ser Ser Leu Arg Glu Ala Leu Ser Phe Val Ser Leu
        355                 360                 365
Ile Asp Gly Tyr Tyr Arg Leu Thr Ala Asp Ala His His Tyr Leu Cys
    370                 375                 380
Lys Glu Val Ala Pro Pro Ala Val Leu Glu Asn Ile Gln Ser Asn Cys
385                 390                 395                 400
His Gly Pro Ile Ser Met Asp Phe Ala Ile Ser Lys Leu Lys Lys Ala
                405                 410                 415
Gly Asn Gln Thr Gly Leu Tyr Val Leu Arg Cys Ser Pro Lys Asp Phe
            420                 425                 430
Asn Lys Tyr Phe Leu Thr Phe Ala Val Glu Arg Glu Asn Val Ile Glu
        435                 440                 445
Tyr Lys His Cys Leu Ile Thr Lys Asn Glu Asn Glu Glu Tyr Asn Leu
    450                 455                 460
Ser Gly Thr Lys Lys Asn Phe Ser Ser Leu Lys Asp Leu Leu Asn Cys
465                 470                 475                 480
Tyr Gln Met Glu Thr Val Arg Ser Asp Asn Ile Ile Phe Gln Phe Thr
                485                 490                 495
Lys Cys Cys Pro Pro Lys Pro Lys Asp Lys Ser Asn Leu Leu Val Phe
            500                 505                 510
Arg Thr Asn Gly Val Ser Asp Val Pro Thr Ser Pro Thr Leu Gln Arg
        515                 520                 525
Pro Thr His Met Asn Gln Met Val Phe His Lys Ile Arg Asn Glu Asp
    530                 535                 540
Leu Ile Phe Asn Glu Ser Leu Gly Gln Gly Thr Phe Thr Lys Ile Phe
545                 550                 555                 560
Lys Gly Val Arg Arg Glu Val Gly Asp Tyr Gly Gln Leu His Glu Thr
                565                 570                 575
Glu Val Leu Leu Lys Val Leu Asp Lys Ala His Arg Asn Tyr Ser Glu
            580                 585                 590
Ser Phe Phe Glu Ala Ala Ser Met Met Ser Lys Leu Ser His Lys His
        595                 600                 605
Leu Val Leu Asn Tyr Gly Val Cys Val Cys Gly Asp Glu Asn Ile Leu
    610                 615                 620
```

-continued

```
Val Gln Glu Phe Val Lys Phe Gly Ser Leu Asp Thr Tyr Leu Lys Lys
625                 630                 635                 640

Asn Lys Asn Cys Ile Asn Ile Leu Trp Lys Leu Val Ala Lys Gln
        645                 650                 655

Leu Ala Trp Ala Met His Phe Leu Glu Glu Asn Thr Leu Ile His Gly
660                 665                 670

Asn Val Cys Ala Lys Asn Ile Leu Leu Ile Arg Glu Glu Asp Arg Lys
            675                 680                 685

Thr Gly Asn Pro Pro Phe Ile Lys Leu Ser Asp Pro Gly Ile Ser Ile
690                 695                 700

Thr Val Leu Pro Lys Asp Ile Leu Gln Glu Arg Ile Pro Trp Val Pro
705                 710                 715                 720

Pro Glu Cys Ile Glu Asn Pro Lys Asn Leu Asn Leu Ala Thr Asp Lys
                725                 730                 735

Trp Ser Phe Gly Thr Thr Leu Trp Glu Ile Cys Ser Gly Gly Asp Lys
            740                 745                 750

Pro Leu Ser Ala Leu Asp Ser Gln Arg Lys Leu Gln Phe Tyr Glu Asp
        755                 760                 765

Arg His Gln Leu Pro Ala Pro Lys Trp Ala Glu Leu Ala Asn Leu Ile
770                 775                 780

Asn Asn Cys Met Asp Tyr Glu Pro Asp Phe Arg Pro Ser Phe Arg Ala
785                 790                 795                 800

Ile Ile Arg Asp Leu Asn Ser Leu Phe Thr Pro Asp Tyr Glu Leu Leu
                805                 810                 815

Thr Glu Asn Asp Met Leu Pro Asn Met Arg Ile Gly Ala Leu Gly Phe
            820                 825                 830

Ser Gly Ala Phe Glu Asp Arg Asp Pro Thr Gln Phe Glu Glu Arg His
        835                 840                 845

Leu Lys Phe Leu Gln Gln Leu Gly Lys Gly Asn Phe Gly Ser Val Glu
850                 855                 860

Met Cys Arg Tyr Asp Pro Leu Gln Asp Asn Thr Gly Glu Val Val Ala
865                 870                 875                 880

Val Lys Lys Leu Gln His Ser Thr Glu Glu His Leu Arg Asp Phe Glu
                885                 890                 895

Arg Glu Ile Glu Ile Leu Lys Ser Leu Gln His Asp Asn Ile Val Lys
            900                 905                 910

Tyr Lys Gly Val Cys Tyr Ser Ala Gly Arg Arg Asn Leu Lys Leu Ile
        915                 920                 925

Met Glu Tyr Leu Pro Tyr Gly Ser Leu Arg Asp Tyr Leu Gln Lys His
930                 935                 940

Lys Glu Arg Ile Asp His Ile Lys Leu Leu Gln Tyr Thr Ser Gln Ile
945                 950                 955                 960

Cys Lys Gly Met Glu Tyr Leu Gly Thr Lys Arg Tyr Ile His Arg Asp
                965                 970                 975

Leu Ala Thr Arg Asn Ile Leu Val Glu Asn Glu Asn Arg Val Lys Ile
            980                 985                 990

Gly Asp Phe Gly Leu Thr Lys Val Leu Pro Gln Asp Lys Glu Tyr Tyr
        995                 1000                1005

Lys Val Lys Glu Pro Gly Glu Ser Pro Ile Phe Trp Tyr Ala Pro
    1010                1015                1020

Glu Ser Leu Thr Glu Ser Lys Phe Ser Val Ala Ser Asp Val Trp
    1025                1030                1035

Ser Phe Gly Val Val Leu Tyr Glu Leu Phe Thr Tyr Ile Glu Lys
```

```
                  1040                1045                1050

Ser Lys Ser Pro Ala Glu Phe Met Arg Met Ile Gly Asn Asp
    1055                1060                1065

Lys Gln Gly Gln Met Ile Val Phe His Leu Ile Glu Leu Leu Lys
1070                1075                1080

Asn Asn Gly Arg Leu Pro Arg Pro Asp Gly Cys Pro Asp Glu Ile
        1085                1090                1095

Tyr Met Ile Met Thr Glu Cys Trp Asn Asn Val Asn Gln Arg
    1100                1105                1110

Pro Ser Phe Arg Asp Leu Ala Leu Arg Val Asp Gln Ile Arg Asp
        1115                1120                1125

Asn Met Ala Gly
        1130

<210> SEQ ID NO 3
<211> LENGTH: 1124
<212> TYPE: PRT
<213> ORGANISM: Homo sapiens

<400> SEQUENCE: 3

Met Ala Pro Pro Ser Glu Glu Thr Pro Leu Ile Pro Gln Arg Ser Cys
1               5                   10                  15

Ser Leu Leu Ser Thr Glu Ala Gly Ala Leu His Val Leu Leu Pro Ala
                20                  25                  30

Arg Gly Pro Gly Pro Pro Gln Arg Leu Ser Phe Ser Phe Gly Asp His
            35                  40                  45

Leu Ala Glu Asp Leu Cys Val Gln Ala Ala Lys Ala Ser Gly Ile Leu
        50                  55                  60

Pro Val Tyr His Ser Leu Phe Ala Leu Ala Thr Glu Asp Leu Ser Cys
65                  70                  75                  80

Trp Phe Pro Pro Ser His Ile Phe Ser Val Glu Asp Ala Ser Thr Gln
                85                  90                  95

Val Leu Leu Tyr Arg Ile Arg Phe Tyr Phe Pro Asn Trp Phe Gly Leu
                100                 105                 110

Glu Lys Cys His Arg Phe Gly Leu Arg Lys Asp Leu Ala Ser Ala Ile
            115                 120                 125

Leu Asp Leu Pro Val Leu Glu His Leu Phe Ala Gln His Arg Ser Asp
        130                 135                 140

Leu Val Ser Gly Arg Leu Pro Val Gly Leu Ser Leu Lys Glu Gln Gly
145                 150                 155                 160

Glu Cys Leu Ser Leu Ala Val Leu Asp Leu Ala Arg Met Ala Arg Glu
                165                 170                 175

Gln Ala Gln Arg Pro Gly Glu Leu Leu Lys Thr Val Ser Tyr Lys Ala
            180                 185                 190

Cys Leu Pro Pro Ser Leu Arg Asp Leu Ile Gln Gly Leu Ser Phe Val
        195                 200                 205

Thr Arg Arg Arg Ile Arg Arg Thr Val Arg Arg Ala Leu Arg Arg Val
        210                 215                 220

Ala Ala Cys Gln Ala Asp Arg His Ser Leu Met Ala Lys Tyr Ile Met
225                 230                 235                 240

Asp Leu Glu Arg Leu Asp Pro Ala Gly Ala Ala Glu Thr Phe His Val
                245                 250                 255

Gly Leu Pro Gly Ala Leu Gly Gly His Asp Gly Leu Gly Leu Leu Arg
            260                 265                 270

Val Ala Gly Asp Gly Gly Ile Ala Trp Thr Gln Gly Glu Gln Glu Val
```

-continued

```
                275                 280                 285
Leu Gln Pro Phe Cys Asp Phe Pro Glu Ile Val Asp Ile Ser Ile Lys
290                 295                 300

Gln Ala Pro Arg Val Gly Pro Ala Gly Glu His Arg Leu Val Thr Val
305                 310                 315                 320

Thr Arg Thr Asp Asn Gln Ile Leu Glu Ala Glu Phe Pro Gly Leu Pro
                325                 330                 335

Glu Ala Leu Ser Phe Val Ala Leu Val Asp Gly Tyr Phe Arg Leu Thr
                340                 345                 350

Thr Asp Ser Gln His Phe Phe Cys Lys Glu Val Ala Pro Pro Arg Leu
                355                 360                 365

Leu Glu Glu Val Ala Glu Gln Cys His Gly Pro Ile Thr Leu Asp Phe
370                 375                 380

Ala Ile Asn Lys Leu Lys Thr Gly Gly Ser Arg Pro Gly Ser Tyr Val
385                 390                 395                 400

Leu Arg Arg Ser Pro Gln Asp Phe Asp Ser Phe Leu Leu Thr Val Cys
                405                 410                 415

Val Gln Asn Pro Leu Gly Pro Asp Tyr Lys Gly Cys Leu Ile Arg Arg
                420                 425                 430

Ser Pro Thr Gly Thr Phe Leu Leu Val Gly Leu Ser Arg Pro His Ser
                435                 440                 445

Ser Leu Arg Glu Leu Leu Ala Thr Cys Trp Asp Gly Gly Leu His Val
450                 455                 460

Asp Gly Val Ala Val Thr Leu Thr Ser Cys Cys Ile Pro Arg Pro Lys
465                 470                 475                 480

Glu Lys Ser Asn Leu Ile Val Val Gln Arg Gly His Ser Pro Pro Thr
                485                 490                 495

Ser Ser Leu Val Gln Pro Gln Ser Gln Tyr Gln Leu Ser Gln Met Thr
                500                 505                 510

Phe His Lys Ile Pro Ala Asp Ser Leu Glu Trp His Glu Asn Leu Gly
                515                 520                 525

His Gly Ser Phe Thr Lys Ile Tyr Arg Gly Cys Arg His Glu Val Val
                530                 535                 540

Asp Gly Glu Ala Arg Lys Thr Glu Val Leu Leu Lys Val Met Asp Ala
545                 550                 555                 560

Lys His Lys Asn Cys Met Glu Ser Phe Leu Glu Ala Ala Ser Leu Met
                565                 570                 575

Ser Gln Val Ser Tyr Arg His Leu Val Leu Leu His Gly Val Cys Met
                580                 585                 590

Ala Gly Asp Ser Thr Met Val Gln Glu Phe Val His Leu Gly Ala Ile
                595                 600                 605

Asp Met Tyr Leu Arg Lys Arg Gly His Leu Val Pro Ala Ser Trp Lys
610                 615                 620

Leu Gln Val Val Lys Gln Leu Ala Tyr Ala Leu Asn Tyr Leu Glu Asp
625                 630                 635                 640

Lys Gly Leu Pro His Gly Asn Val Ser Ala Arg Lys Val Leu Leu Ala
                645                 650                 655

Arg Glu Gly Ala Asp Gly Ser Pro Pro Phe Ile Lys Leu Ser Asp Pro
                660                 665                 670

Gly Val Ser Pro Ala Val Leu Ser Leu Glu Met Leu Thr Asp Arg Ile
                675                 680                 685

Pro Trp Val Ala Pro Glu Cys Leu Arg Glu Ala Gln Thr Leu Ser Leu
690                 695                 700
```

-continued

Glu Ala Asp Lys Trp Gly Phe Gly Ala Thr Val Trp Glu Val Phe Ser
705                 710                 715                 720

Gly Val Thr Met Pro Ile Ser Ala Leu Asp Pro Ala Lys Lys Leu Gln
            725                 730                 735

Phe Tyr Glu Asp Arg Gln Gln Leu Pro Ala Pro Lys Trp Thr Glu Leu
        740                 745                 750

Ala Leu Leu Ile Gln Gln Cys Met Ala Tyr Glu Pro Val Gln Arg Pro
            755                 760                 765

Ser Phe Arg Ala Val Ile Arg Asp Leu Asn Ser Leu Ile Ser Ser Asp
    770                 775                 780

Tyr Glu Leu Leu Ser Asp Pro Thr Pro Gly Ala Leu Ala Pro Arg Asp
785                 790                 795                 800

Gly Leu Trp Asn Gly Ala Gln Leu Tyr Ala Cys Gln Asp Pro Thr Ile
            805                 810                 815

Phe Glu Glu Arg His Leu Lys Tyr Ile Ser Gln Leu Gly Lys Gly Asn
        820                 825                 830

Phe Gly Ser Val Glu Leu Cys Arg Tyr Asp Pro Leu Gly Asp Asn Thr
            835                 840                 845

Gly Ala Leu Val Ala Val Lys Gln Leu Gln His Ser Gly Pro Asp Gln
850                 855                 860

Gln Arg Asp Phe Gln Arg Glu Ile Gln Ile Leu Lys Ala Leu His Ser
865                 870                 875                 880

Asp Phe Ile Val Lys Tyr Arg Gly Val Ser Tyr Gly Pro Gly Arg Gln
            885                 890                 895

Ser Leu Arg Leu Val Met Glu Tyr Leu Pro Ser Gly Cys Leu Arg Asp
            900                 905                 910

Phe Leu Gln Arg His Arg Ala Arg Leu Asp Ala Ser Arg Leu Leu Leu
        915                 920                 925

Tyr Ser Ser Gln Ile Cys Lys Gly Met Glu Tyr Leu Gly Ser Arg Arg
930                 935                 940

Cys Val His Arg Asp Leu Ala Ala Arg Asn Ile Leu Val Glu Ser Glu
945                 950                 955                 960

Ala His Val Lys Ile Ala Asp Phe Gly Leu Ala Lys Leu Leu Pro Leu
            965                 970                 975

Asp Lys Asp Tyr Tyr Val Val Arg Glu Pro Gly Gln Ser Pro Ile Phe
        980                 985                 990

Trp Tyr Ala Pro Glu Ser Leu Ser Asp Asn Ile Phe Ser Arg Gln Ser
        995                 1000                1005

Asp Val Trp Ser Phe Gly Val Val Leu Tyr Glu Leu Phe Thr Tyr
    1010                1015                1020

Cys Asp Lys Ser Cys Ser Pro Ser Ala Glu Phe Leu Arg Met Met
    1025                1030                1035

Gly Cys Glu Arg Asp Val Pro Ala Leu Cys Arg Leu Leu Glu Leu
    1040                1045                1050

Leu Glu Glu Gly Gln Arg Leu Pro Ala Pro Pro Ala Cys Pro Ala
    1055                1060                1065

Glu Val His Glu Leu Met Lys Leu Cys Trp Ala Pro Ser Pro Gln
    1070                1075                1080

Asp Arg Pro Ser Phe Ser Ala Leu Gly Pro Gln Leu Asp Met Leu
    1085                1090                1095

Trp Ser Gly Ser Arg Gly Cys Glu Thr His Ala Phe Thr Ala His
    1100                1105                1110

Pro Glu Gly Lys His His Ser Leu Ser Phe Ser
    1115                1120

-continued

```
<210> SEQ ID NO 4
<211> LENGTH: 1187
<212> TYPE: PRT
<213> ORGANISM: Homo sapiens

<400> SEQUENCE: 4

Met Pro Leu Arg His Trp Gly Met Ala Arg Gly Ser Lys Pro Val Gly
1               5                   10                  15

Asp Gly Ala Gln Pro Met Ala Ala Met Gly Gly Leu Lys Val Leu Leu
            20                  25                  30

His Trp Ala Gly Pro Gly Gly Gly Glu Pro Trp Val Thr Phe Ser Glu
        35                  40                  45

Ser Ser Leu Thr Ala Glu Glu Val Cys Ile His Ile Ala His Lys Val
50                  55                  60

Gly Ile Thr Pro Pro Cys Phe Asn Leu Phe Ala Leu Phe Asp Ala Gln
65                  70                  75                  80

Ala Gln Val Trp Leu Pro Pro Asn His Ile Leu Glu Ile Pro Arg Asp
                85                  90                  95

Ala Ser Leu Met Leu Tyr Phe Arg Ile Arg Phe Tyr Phe Arg Asn Trp
            100                 105                 110

His Gly Met Asn Pro Arg Glu Pro Ala Val Tyr Arg Cys Gly Pro Pro
        115                 120                 125

Gly Thr Glu Ala Ser Ser Asp Gln Thr Ala Gln Gly Met Gln Leu Leu
130                 135                 140

Asp Pro Ala Ser Phe Glu Tyr Leu Phe Glu Gln Gly Lys His Glu Phe
145                 150                 155                 160

Val Asn Asp Val Ala Ser Leu Trp Glu Leu Ser Thr Glu Glu Glu Ile
                165                 170                 175

His His Phe Lys Asn Glu Ser Leu Gly Met Ala Phe Leu His Leu Cys
            180                 185                 190

His Leu Ala Leu Arg His Gly Ile Pro Leu Glu Glu Val Ala Lys Lys
        195                 200                 205

Thr Ser Phe Lys Asp Cys Ile Pro Arg Ser Phe Arg Arg His Ile Arg
210                 215                 220

Gln His Ser Ala Leu Thr Arg Leu Arg Leu Arg Asn Val Phe Arg Arg
225                 230                 235                 240

Phe Leu Arg Asp Phe Gln Pro Gly Arg Leu Ser Gln Gln Met Val Met
                245                 250                 255

Val Lys Tyr Leu Ala Thr Leu Glu Arg Leu Ala Pro Arg Phe Gly Thr
            260                 265                 270

Glu Arg Val Pro Val Cys His Leu Arg Leu Leu Ala Gln Ala Glu Gly
        275                 280                 285

Glu Pro Cys Tyr Ile Arg Asp Ser Gly Val Ala Pro Thr Asp Pro Gly
290                 295                 300

Pro Glu Ser Ala Ala Gly Pro Pro Thr His Glu Val Leu Val Thr Gly
305                 310                 315                 320

Thr Gly Gly Ile Gln Trp Trp Pro Val Glu Glu Val Asn Lys Glu
                325                 330                 335

Glu Gly Ser Ser Gly Ser Ser Gly Arg Asn Pro Gln Ala Ser Leu Phe
            340                 345                 350

Gly Lys Lys Ala Lys Ala His Lys Ala Val Gly Gln Pro Ala Asp Arg
        355                 360                 365

Pro Arg Glu Pro Leu Trp Ala Tyr Phe Cys Asp Phe Arg Asp Ile Thr
370                 375                 380
```

```
His Val Val Leu Lys Glu His Cys Val Ser Ile His Arg Gln Asp Asn
385                 390                 395                 400

Lys Cys Leu Glu Leu Ser Leu Pro Ser Arg Ala Ala Ala Leu Ser Phe
            405                 410                 415

Val Ser Leu Val Asp Gly Tyr Phe Arg Leu Thr Ala Asp Ser Ser His
        420                 425                 430

Tyr Leu Cys His Glu Val Ala Pro Pro Arg Leu Val Met Ser Ile Arg
            435                 440                 445

Asp Gly Ile His Gly Pro Leu Leu Glu Pro Phe Val Gln Ala Lys Leu
        450                 455                 460

Arg Pro Glu Asp Gly Leu Tyr Leu Ile His Trp Ser Thr Ser His Pro
465                 470                 475                 480

Tyr Arg Leu Ile Leu Thr Val Ala Gln Arg Ser Gln Ala Pro Asp Gly
            485                 490                 495

Met Gln Ser Leu Arg Leu Arg Lys Phe Pro Ile Glu Gln Gln Asp Gly
        500                 505                 510

Ala Phe Val Leu Glu Gly Trp Gly Arg Ser Phe Pro Ser Val Arg Glu
            515                 520                 525

Leu Gly Ala Ala Leu Gln Gly Cys Leu Leu Arg Ala Gly Asp Asp Cys
        530                 535                 540

Phe Ser Leu Arg Arg Cys Cys Leu Pro Gln Pro Gly Glu Thr Ser Asn
545                 550                 555                 560

Leu Ile Ile Met Arg Gly Ala Arg Ala Ser Pro Arg Thr Leu Asn Leu
            565                 570                 575

Ser Gln Leu Ser Phe His Arg Val Asp Gln Lys Glu Ile Thr Gln Leu
        580                 585                 590

Ser His Leu Gly Gln Gly Thr Arg Thr Asn Val Tyr Glu Gly Arg Leu
    595                 600                 605

Arg Val Glu Gly Ser Gly Asp Pro Glu Glu Gly Lys Met Asp Asp Glu
        610                 615                 620

Asp Pro Leu Val Pro Gly Arg Asp Arg Gly Gln Glu Leu Arg Val Val
625                 630                 635                 640

Leu Lys Val Leu Asp Pro Ser His His Asp Ile Ala Leu Ala Phe Tyr
            645                 650                 655

Glu Thr Ala Ser Leu Met Ser Gln Val Ser His Thr His Leu Ala Phe
        660                 665                 670

Val His Gly Val Cys Val Arg Gly Pro Glu Asn Ile Met Val Thr Glu
    675                 680                 685

Tyr Val Glu His Gly Pro Leu Asp Val Trp Leu Arg Arg Glu Arg Gly
        690                 695                 700

His Val Pro Met Ala Trp Lys Met Val Val Ala Gln Gln Leu Ala Ser
705                 710                 715                 720

Ala Leu Ser Tyr Leu Glu Asn Lys Asn Leu Val His Gly Asn Val Cys
            725                 730                 735

Gly Arg Asn Ile Leu Leu Ala Arg Leu Gly Leu Ala Glu Gly Thr Ser
        740                 745                 750

Pro Phe Ile Lys Leu Ser Asp Pro Gly Val Gly Leu Gly Ala Leu Ser
        755                 760                 765

Arg Glu Glu Arg Val Glu Arg Ile Pro Trp Leu Ala Pro Glu Cys Leu
        770                 775                 780

Pro Gly Gly Ala Asn Ser Leu Ser Thr Ala Met Asp Lys Trp Gly Phe
785                 790                 795                 800

Gly Ala Thr Leu Leu Glu Ile Cys Phe Asp Gly Glu Ala Pro Leu Gln
```

-continued

```
                          805                 810                 815
Ser Arg Ser Pro Ser Glu Lys Glu His Phe Tyr Gln Arg Gln His Arg
                820                 825                 830

Leu Pro Glu Pro Ser Cys Pro Gln Leu Ala Thr Leu Thr Ser Gln Cys
            835                 840                 845

Leu Thr Tyr Glu Pro Thr Gln Arg Pro Ser Phe Arg Thr Ile Leu Arg
        850                 855                 860

Asp Leu Thr Arg Leu Gln Pro His Asn Leu Ala Asp Val Leu Thr Val
    865                 870                 875                 880

Asn Pro Asp Ser Pro Ala Ser Asp Pro Thr Val Phe His Lys Arg Tyr
                885                 890                 895

Leu Lys Lys Ile Arg Asp Leu Gly Glu Gly His Phe Gly Lys Val Ser
            900                 905                 910

Leu Tyr Cys Tyr Asp Pro Thr Asn Asp Gly Thr Gly Glu Met Val Ala
        915                 920                 925

Val Lys Ala Leu Lys Ala Asp Cys Gly Pro Gln His Arg Ser Gly Trp
    930                 935                 940

Lys Gln Glu Ile Asp Ile Leu Arg Thr Leu Tyr His Glu His Ile Ile
945                 950                 955                 960

Lys Tyr Lys Gly Cys Cys Glu Asp Gln Gly Glu Lys Ser Leu Gln Leu
                965                 970                 975

Val Met Glu Tyr Val Pro Leu Gly Ser Leu Arg Asp Tyr Leu Pro Arg
            980                 985                 990

His Ser Ile Gly Leu Ala Gln Leu Leu Leu Phe Ala Gln Gln Ile Cys
        995                 1000                1005

Glu Gly Met Ala Tyr Leu His Ala Gln His Tyr Ile His Arg Asp
    1010                1015                1020

Leu Ala Ala Arg Asn Val Leu Leu Asp Asn Asp Arg Leu Val Lys
    1025                1030                1035

Ile Gly Asp Phe Gly Leu Ala Lys Ala Val Pro Glu Gly His Glu
    1040                1045                1050

Tyr Tyr Arg Val Arg Glu Asp Gly Asp Ser Pro Val Phe Trp Tyr
    1055                1060                1065

Ala Pro Glu Cys Leu Lys Glu Tyr Lys Phe Tyr Tyr Ala Ser Asp
    1070                1075                1080

Val Trp Ser Phe Gly Val Thr Leu Tyr Glu Leu Leu Thr His Cys
    1085                1090                1095

Asp Ser Ser Gln Ser Pro Pro Thr Lys Phe Leu Glu Leu Ile Gly
    1100                1105                1110

Ile Ala Gln Gly Gln Met Thr Val Leu Arg Leu Thr Glu Leu Leu
    1115                1120                1125

Glu Arg Gly Glu Arg Leu Pro Arg Pro Asp Lys Cys Pro Cys Glu
    1130                1135                1140

Val Tyr His Leu Met Lys Asn Cys Trp Glu Thr Glu Ala Ser Phe
    1145                1150                1155

Arg Pro Thr Phe Glu Asn Leu Ile Pro Ile Leu Lys Thr Val His
    1160                1165                1170

Glu Lys Tyr Gln Gly Gln Ala Pro Ser Val Phe Ser Val Cys
    1175                1180                1185

<210> SEQ ID NO 5
<211> LENGTH: 22
<212> TYPE: PRT
<213> ORGANISM: Artificial Sequence
<220> FEATURE:
```

-continued

```
<223> OTHER INFORMATION: Synthetic Construct

<400> SEQUENCE: 5

Lys Thr Glu Val Asn Leu Glu Ala Pro Glu Pro Gly Val Glu Val Ile
1               5                   10                  15

Phe Tyr Leu Ser Asp Arg
            20

<210> SEQ ID NO 6
<211> LENGTH: 14
<212> TYPE: PRT
<213> ORGANISM: Artificial Sequence
<220> FEATURE:
<223> OTHER INFORMATION: Synthetic Construct

<400> SEQUENCE: 6

Leu Gly Ser Gly Glu Tyr Thr Ala Glu Glu Leu Cys Ile Arg
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Synthetic Construct

<400> SEQUENCE: 7

Lys Gln Ile Leu Arg Thr Asp Asn Ile Ser Phe Met Leu Lys Arg
1               5                   10                  15

<210> SEQ ID NO 8
<211> LENGTH: 13
<212> TYPE: PRT
<213> ORGANISM: Artificial Sequence
<220> FEATURE:
<223> OTHER INFORMATION: Synthetic Construct

<400> SEQUENCE: 8

Leu Ser Asp Pro Gly Ile Pro Ile Thr Val Leu Ser Arg
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic Construct

<400> SEQUENCE: 9

Ile Pro Trp Ile Ala Pro Glu Cys Val Glu Asp Ser Lys
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Synthetic Construct

<400> SEQUENCE: 10

Lys Pro Ala Thr Glu Val Asp Pro Thr His Phe Glu Lys
1               5                   10

<210> SEQ ID NO 11
<211> LENGTH: 11
<212> TYPE: PRT
<213> ORGANISM: Artificial Sequence
```

```
<220> FEATURE:
<223> OTHER INFORMATION: Synthetic Construct

<400> SEQUENCE: 11

Ile Arg Asp Leu Gly Glu Gly His Phe Gly Lys
1               5                   10

<210> SEQ ID NO 12
<211> LENGTH: 31
<212> TYPE: PRT
<213> ORGANISM: Artificial Sequence
<220> FEATURE:
<223> OTHER INFORMATION: Synthetic Construct

<400> SEQUENCE: 12

Tyr Asp Pro Glu Gly Asp Asn Thr Gly Glu Gln Val Ala Val Lys Ser
1               5                   10                  15

Leu Lys Pro Glu Ser Gly Gly Asn His Ile Ala Asp Leu Lys Lys
            20                  25                  30

<210> SEQ ID NO 13
<211> LENGTH: 19
<212> TYPE: PRT
<213> ORGANISM: Artificial Sequence
<220> FEATURE:
<223> OTHER INFORMATION: Synthetic Construct

<400> SEQUENCE: 13

Asn Val Leu Val Glu Ser Glu His Gln Val Lys Ile Gly Asp Phe Gly
1               5                   10                  15

Leu Thr Lys

<210> SEQ ID NO 14
<211> LENGTH: 6
<212> TYPE: PRT
<213> ORGANISM: Artificial Sequence
<220> FEATURE:
<223> OTHER INFORMATION: Synthetic Construct

<400> SEQUENCE: 14

His Asn Val Leu Tyr Arg
1               5

<210> SEQ ID NO 15
<211> LENGTH: 16
<212> TYPE: PRT
<213> ORGANISM: Artificial Sequence
<220> FEATURE:
<223> OTHER INFORMATION: Synthetic Construct

<400> SEQUENCE: 15

Glu Asn Asp Gln Thr Pro Leu Ala Ile Tyr Asn Ser Ile Ser Tyr Lys
1               5                   10                  15

<210> SEQ ID NO 16
<211> LENGTH: 9
<212> TYPE: PRT
<213> ORGANISM: Artificial Sequence
<220> FEATURE:
<223> OTHER INFORMATION: Synthetic Construct

<400> SEQUENCE: 16

Phe Ile Gln Gln Phe Ser Gln Cys Lys
1               5

<210> SEQ ID NO 17
```

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 17

Asn Leu Glu Ile Glu Leu Ser Ser Leu Arg
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthetic Construct

<400> SEQUENCE: 18

Leu Thr Ala Asp Ala His His Tyr Leu Cys Lys
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Synthetic Construct

<400> SEQUENCE: 19

Tyr Phe Leu Thr Phe Ala Val Glu Arg
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic Construct

<400> SEQUENCE: 20

Ser Asp Asn Ile Ile Phe Gln Phe Thr Lys
1               5                   10

<210> SEQ ID NO 21
<211> LENGTH: 16
<212> TYPE: PRT
<213> ORGANISM: Artificial Sequence
<220> FEATURE:
<223> OTHER INFORMATION: Synthetic Construct

<400> SEQUENCE: 21

Glu Val Gly Asp Tyr Gly Gln Leu His Glu Thr Glu Val Leu Leu Lys
1               5                   10                  15

<210> SEQ ID NO 22
<211> LENGTH: 8
<212> TYPE: PRT
<213> ORGANISM: Artificial Sequence
<220> FEATURE:
<223> OTHER INFORMATION: Synthetic Construct

<400> SEQUENCE: 22

Thr Gly Asn Pro Pro Phe Ile Lys
1               5

<210> SEQ ID NO 23
<211> LENGTH: 13
<212> TYPE: PRT
```

```
<213> ORGANISM: Artificial Sequence
<220> FEATURE:
<223> OTHER INFORMATION: Synthetic Construct

<400> SEQUENCE: 23

Ile Pro Trp Val Pro Pro Glu Cys Ile Glu Asn Pro Lys
1               5                   10

<210> SEQ ID NO 24
<211> LENGTH: 21
<212> TYPE: PRT
<213> ORGANISM: Artificial Sequence
<220> FEATURE:
<223> OTHER INFORMATION: Synthetic Construct

<400> SEQUENCE: 24

Ile Gly Ala Leu Gly Phe Ser Gly Ala Phe Glu Asp Arg Asp Pro Thr
1               5                   10                  15

Gln Phe Glu Glu Arg
            20

<210> SEQ ID NO 25
<211> LENGTH: 25
<212> TYPE: PRT
<213> ORGANISM: Artificial Sequence
<220> FEATURE:
<223> OTHER INFORMATION: Synthetic Construct

<400> SEQUENCE: 25

Gly Asn Phe Gly Ser Val Glu Met Cys Arg Tyr Asp Pro Leu Gln Asp
1               5                   10                  15

Asn Thr Gly Glu Val Val Ala Val Lys
            20                  25

<210> SEQ ID NO 26
<211> LENGTH: 9
<212> TYPE: PRT
<213> ORGANISM: Artificial Sequence
<220> FEATURE:
<223> OTHER INFORMATION: Synthetic Construct

<400> SEQUENCE: 26

Ser Leu Gln His Asp Asn Ile Val Lys
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic Construct

<400> SEQUENCE: 27

Gly Val Cys Tyr Ser Ala Gly Arg
1               5

<210> SEQ ID NO 28
<211> LENGTH: 12
<212> TYPE: PRT
<213> ORGANISM: Artificial Sequence
<220> FEATURE:
<223> OTHER INFORMATION: Synthetic Construct

<400> SEQUENCE: 28

Leu Ile Met Glu Tyr Leu Pro Tyr Gly Ser Leu Arg
1               5                   10
```

```
<210> SEQ ID NO 29
<211> LENGTH: 10
<212> TYPE: PRT
<213> ORGANISM: Artificial Sequence
<220> FEATURE:
<223> OTHER INFORMATION: Synthetic Construct

<400> SEQUENCE: 29

Leu Leu Gln Tyr Thr Ser Gln Ile Cys Lys
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthetic Construct

<400> SEQUENCE: 30

Val Leu Pro Gln Asp Lys Glu Tyr Tyr Lys
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Synthetic Construct

<400> SEQUENCE: 31

Val Asp Gln Ile Arg Asp Asn Met Ala Gly
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic Construct

<400> SEQUENCE: 32

Phe Tyr Phe Pro Asn Trp Phe Gly Leu Glu Lys
1               5                   10

<210> SEQ ID NO 33
<211> LENGTH: 9
<212> TYPE: PRT
<213> ORGANISM: Artificial Sequence
<220> FEATURE:
<223> OTHER INFORMATION: Synthetic Construct

<400> SEQUENCE: 33

His Glu Val Val Asp Gly Glu Ala Arg
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic Construct

<400> SEQUENCE: 34

Gly His Leu Val Pro Ala Ser Trp Lys
1               5

<210> SEQ ID NO 35
```

```
<211> LENGTH: 11
<212> TYPE: PRT
<213> ORGANISM: Artificial Sequence
<220> FEATURE:
<223> OTHER INFORMATION: Synthetic Construct

<400> SEQUENCE: 35

Gln Leu Gln His Ser Gly Pro Asp Gln Gln Arg
1               5                   10

<210> SEQ ID NO 36
<211> LENGTH: 18
<212> TYPE: PRT
<213> ORGANISM: Artificial Sequence
<220> FEATURE:
<223> OTHER INFORMATION: Synthetic Construct

<400> SEQUENCE: 36

Leu Leu Leu Tyr Ser Ser Gln Ile Cys Lys Gly Met Glu Tyr Leu Gly
1               5                   10                  15

Ser Arg

<210> SEQ ID NO 37
<211> LENGTH: 10
<212> TYPE: PRT
<213> ORGANISM: Artificial Sequence
<220> FEATURE:
<223> OTHER INFORMATION: Synthetic Construct

<400> SEQUENCE: 37

Ser Cys Ser Pro Ser Ala Glu Phe Leu Arg
1               5                   10

<210> SEQ ID NO 38
<211> LENGTH: 21
<212> TYPE: PRT
<213> ORGANISM: Artificial Sequence
<220> FEATURE:
<223> OTHER INFORMATION: Synthetic Construct

<400> SEQUENCE: 38

Ala Val Gly Gln Pro Ala Asp Arg Pro Arg Glu Pro Leu Trp Ala Tyr
1               5                   10                  15

Phe Cys Asp Phe Arg
                20

<210> SEQ ID NO 39
<211> LENGTH: 15
<212> TYPE: PRT
<213> ORGANISM: Artificial Sequence
<220> FEATURE:
<223> OTHER INFORMATION: Synthetic Construct

<400> SEQUENCE: 39

Ala Ala Ala Leu Ser Phe Val Ser Leu Val Asp Gly Tyr Phe Arg
1               5                   10                  15
```

```
<210> SEQ ID NO 40
<211> LENGTH: 15
<212> TYPE: PRT
<213> ORGANISM: Artificial Sequence
<220> FEATURE:
<223> OTHER INFORMATION: Synthetic Construct

<400> SEQUENCE: 40

Asp Gly Ile His Gly Pro Leu Leu Glu Pro Phe Val Gln Ala Lys
1               5                   10                  15

<210> SEQ ID NO 41
<211> LENGTH: 19
<212> TYPE: PRT
<213> ORGANISM: Artificial Sequence
<220> FEATURE:
<223> OTHER INFORMATION: Synthetic Construct

<400> SEQUENCE: 41

Leu Ile Leu Thr Val Ala Gln Arg Ser Gln Ala Pro Asp Gly Met Gln
1               5                   10                  15

Ser Leu Arg

<210> SEQ ID NO 42
<211> LENGTH: 18
<212> TYPE: PRT
<213> ORGANISM: Artificial Sequence
<220> FEATURE:
<223> OTHER INFORMATION: Synthetic Construct

<400> SEQUENCE: 42

Lys Phe Pro Ile Glu Gln Gln Asp Gly Ala Phe Val Leu Glu Gly Trp
1               5                   10                  15

Gly Arg

<210> SEQ ID NO 43
<211> LENGTH: 7
<212> TYPE: PRT
<213> ORGANISM: Artificial Sequence
<220> FEATURE:
<223> OTHER INFORMATION: Synthetic Construct

<400> SEQUENCE: 43

Thr Asn Val Tyr Glu Gly Arg
1               5

<210> SEQ ID NO 44
<211> LENGTH: 17
<212> TYPE: PRT
<213> ORGANISM: Artificial Sequence
<220> FEATURE:
<223> OTHER INFORMATION: Synthetic Construct

<400> SEQUENCE: 44

Met Val Val Ala Gln Gln Leu Ala Ser Ala Leu Ser Tyr Leu Glu Asn
1               5                   10                  15

Lys

<210> SEQ ID NO 45
<211> LENGTH: 25
<212> TYPE: PRT
<213> ORGANISM: Artificial Sequence
<220> FEATURE:
<223> OTHER INFORMATION: Synthetic Construct

<400> SEQUENCE: 45
```

```
Leu Gly Leu Ala Glu Gly Thr Ser Pro Phe Ile Lys Leu Ser Asp Pro
1               5                   10                  15

Gly Val Gly Leu Gly Ala Leu Ser Arg
            20                  25

<210> SEQ ID NO 46
<211> LENGTH: 11
<212> TYPE: PRT
<213> ORGANISM: Artificial Sequence
<220> FEATURE:
<223> OTHER INFORMATION: Synthetic Construct

<400> SEQUENCE: 46

Ser Pro Ser Glu Lys Glu His Phe Tyr Gln Arg
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Synthetic Construct

<400> SEQUENCE: 47

Ile Arg Asp Leu Gly Glu Gly His Phe Gly Lys
1               5                   10

<210> SEQ ID NO 48
<211> LENGTH: 8
<212> TYPE: PRT
<213> ORGANISM: Artificial Sequence
<220> FEATURE:
<223> OTHER INFORMATION: Synthetic Construct

<400> SEQUENCE: 48

Ile Gly Asp Phe Gly Leu Ala Lys
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic Construct

<400> SEQUENCE: 49

Leu Thr Glu Leu Leu Glu Arg
1               5

<210> SEQ ID NO 50
<211> LENGTH: 12
<212> TYPE: PRT
<213> ORGANISM: Artificial Sequence
<220> FEATURE:
<223> OTHER INFORMATION: Synthetic Construct

<400> SEQUENCE: 50

Tyr Gln Gly Gln Ala Pro Ser Val Phe Ser Val Cys
1               5                   10
```